United States Patent
Serhan et al.

(10) Patent No.: US 11,592,453 B2
(45) Date of Patent: Feb. 28, 2023

(54) PERSONALIZED METABOLOMIC PROFILING OF SPECIALIZED PRO-RESOLVING MEDIATORS

(71) Applicant: THE BRIGHAM AND WOMEN'S HOSPITAL, INC., Boston, MA (US)

(72) Inventors: Charles N. Serhan, Needham, MA (US); Nan Chiang, Boston, MA (US); Paul Norris, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 855 days.

(21) Appl. No.: 16/462,523

(22) PCT Filed: Nov. 22, 2017

(86) PCT No.: PCT/US2017/062966
§ 371 (c)(1),
(2) Date: May 20, 2019

(87) PCT Pub. No.: WO2018/098244
PCT Pub. Date: May 31, 2018

(65) Prior Publication Data
US 2019/0346462 A1 Nov. 14, 2019

Related U.S. Application Data

(60) Provisional application No. 62/425,367, filed on Nov. 22, 2016.

(51) Int. Cl.
*G01N 33/86* (2006.01)
*A61B 5/15* (2006.01)
*G01N 30/72* (2006.01)
*G01N 33/92* (2006.01)
*G01N 33/96* (2006.01)
*G01N 30/02* (2006.01)

(52) U.S. Cl.
CPC ....... *G01N 33/86* (2013.01); *A61B 5/150755* (2013.01); *G01N 30/7233* (2013.01); *G01N 33/92* (2013.01); *G01N 33/96* (2013.01); *G01N 2030/027* (2013.01)

(58) Field of Classification Search
CPC ........ G01N 33/86; G01N 33/92; G01N 33/96; A61B 5/150755
See application file for complete search history.

(56) References Cited

U.S. PATENT DOCUMENTS

| | | |
|---|---|---|
| 2003/0032827 A1 | 2/2003 | Serhan |
| 2005/0026296 A1 | 2/2005 | Baenkler |
| 2008/0254146 A1 | 10/2008 | Huey |
| 2016/0115112 A1 | 4/2016 | Serhan et al. |

FOREIGN PATENT DOCUMENTS

| | | |
|---|---|---|
| WO | 2014039964 | 3/2014 |
| WO | 2016057700 | 4/2016 |

OTHER PUBLICATIONS

Colas et al. Identification and Signature Profiles for Pro-Resolving and Inflammatory Lipid Mediators in Human Tissue; American Journal of Physiology-Cell Physiology, vol. 307, pp. C39-C54. (Year: 2014).*
Alfrasabian et al. Diagnostic Value of Serum Adenosine Deaminase Level in Pulmonary Tuberculosis; Journal of Research in Medical Sciences, vol. 18, No. 3 pp. 252-254. (Year: 2013).*
Alrokayan, S. Purification and Characterization of Adenosine Deaminase From Camel Skeletal Muscle; The International Journal of Biochemistry and Cell Biology, vol. 34, pp. 1608-1618. (Year: 2002).*
Kuno et al. Anti-Inflammatory Activity of Non-Nucleoside Adenosine Deaminase Inhibitor FR234938; European Journal of Pharmacology, vol. 534, pp. 241-249. (Year: 2006).*
Shu et al. Relation of Enzyme Activity To Local/Global Stability of Murine Adenosine Deaminase: 19FNMR Studies; Journal of Molecular Biology, vol. 345, No. 3, pp. 599-610. (Year: 2005).*
Dalli et al. The Regulation of Proresolving Lipid Mediator Profiles in Baboon Pneumonia By Inhaled Carbon Monoxide; American Journal of Respiratory Cell and Molecular Biology, vol. 53, No. 3, pp. 314-325. (Year: 2015).*
Wu, Y. Contact Pathway of Coagulation and Inflammation; Thrombosis Journal, vol. 13, No. 17, pp. 1-9. (Year: 2015).*
Pillai et al. Chemical Mediators of Inflammation and Resolution in Post-Operative Abdominal Aortic Aneurysm Patients; Inflammation, vol. 35, No. 1, pp. 98-113. (Year: 2012).*
Elajami et al. Specialized Proresolving Lipid Mediators in Patients With Coronary Artery Disease and Their Potential for Clot Remodeling; The FASEB Journal, vol. 30, pp. 2792-2801. (Year: 2016).*
Barden et al. Specialized Proresolving Lipid Mediators in Humans With the Metabolic Syndrome After N-3 Fatty Acids and Aspirin; American Journal of Clinical Nutrition, vol. 102, pp. 1357-1364. (Year: 2015).*
Bohr, S. et al., Resolvin D2 prevents secondary thrombosis and necrosis in a mouse burn wound model. Wound Repair Regen. 21, 35-43 (2013).

(Continued)

*Primary Examiner* — Neil P Hammell
*Assistant Examiner* — Paul C Martin
(74) *Attorney, Agent, or Firm* — Haukaas Fortius PLLC; Colin L. Fairman

(57) ABSTRACT

Disclosed herein is a method of providing a metabololipidomic profile and SPM signature on the progress of the innate host defense response following blood clotting. The method can include the step of taking one or more measurements in a patient's blood sample, wherein the sample is obtained during the time-course of clotting or coagulation or following clotting or coagulation, of pro-thrombotic and pro-inflammatory mediators (eicosanoids) and specialized pro-resolving mediators SPMs. From these measurements, a personalized metabololipidomic profile can be obtained. By comparing the measurement to that taken from normal or reference blood, a comparison profile can be developed. The profile comparison profile can then be used to make a medical or therapeutic decision.

16 Claims, 22 Drawing Sheets

(56) References Cited

OTHER PUBLICATIONS

Brancaleone, V. et al., A vasculo-protective circuit centred on Lipoxin A4 and aspirin-triggered 15-epi-lipoxin A4 operative in murine microcirculation. Blood, 10.1182/blood-2013-1104-496661 [doi] (2013).

De Caterina, R., n-3 fatty acids in cardiovascular disease. N Engl J Med 364, 2439-2450 (2011).

Del Gobbo, L.C. et al., omega-3 Polyunsaturated Fatty Acid Biomarkers and Coronary Heart Disease: Pooling Project of 19 Cohort Studies. JAMA Intern Med 176, 1155-1166 (2016).

Fredman, G. et al, Specialized proresolving mediator targets for RvE1 and RvD1 in peripheral blood and mechanisms of resolution. Biochem J 437, 185-197 (2011).

Hamberg, M. et al., Thromboxanes: a new group of biologically active compounds derived from prostaglandin endoperoxides. Proc. Natl. Acad. Sci. U. S. A. 72, 2994-2998 (1975).

International Searching Authority, International Search Report & Written Opinion for application PCT/US2017/062966, dated Feb. 16, 2018, 17 pages.

Krump E. et al., Suppression of leukotriene B4 biosynthesis by endogenous adenosine in ligand-activated human neutrophils. J. Exp. Med. 186, 1401-1406 (1997).

Mas, E. et al., Resolvins D1, D2, and other mediators of self-limited resolution of inflammation in human blood following n-3 fatty acid supplementation. Clin. Chem. 58, 1476-1484 (2012).

Pope, N. H. et al., D-series resolvins inhibit murine abdominal aortic aneurysm formation and increase M2 macrophage polarization. FASEB J. 30, 4192-4201 (2016).

Sansbury, B.E., et al., Resolution of Acute Inflammation and the Role of Resolvins in Immunity, Thrombosis, and Vascular Biology. Circ Res 119, 113-130 (2016).

Serhan, C.N. et al., Novel proresolving aspirin-triggered DHA pathway. Chem. Biol. 18, 976-987 (2011).

Topper, J.N. et al., Identification of vascular endothelial genes differentially responsive to fluid mechanical stimuli: Cyclooxygenase-2, manganese superoxide dismutase, and endothelial cell nitric oxide synthase are selectively up-regulated by steady laminar shear stress. Proc. Natl. Acad. Sci USA 93, 10417-10422 (1996).

Extended European Search Report from corresponding European Application No. 17872994.3, 7 pages, dated Jun. 17, 2020.

* cited by examiner

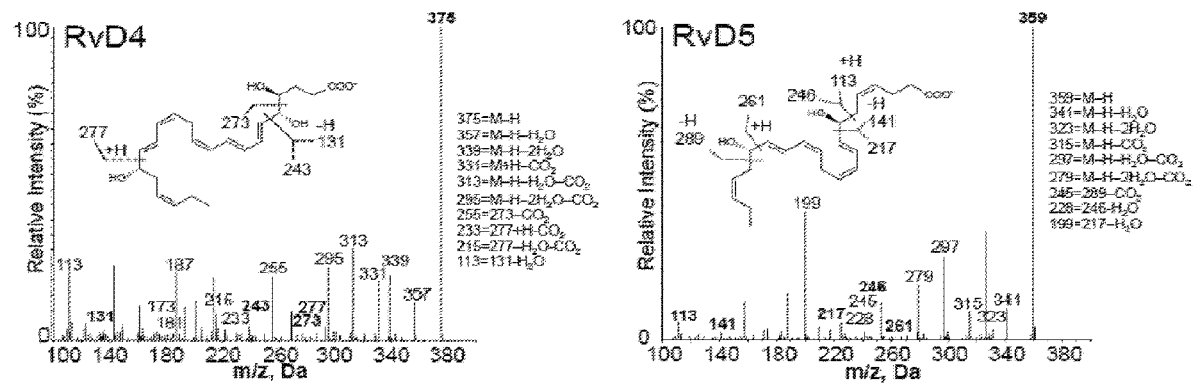
Fig. 11 (COTINUED)

PERSONALIZED METABOLOMIC PROFILING OF SPECIALIZED PRO-RESOLVING MEDIATORS

CROSS-REFERENCE TO RELATED APPLICATIONS

This application represents the national stage entry of international application PCT/US2017/062966, filed Nov. 22, 2017, which claims benefit of U.S. Provisional Application 62/425,367 filed Nov. 22, 2016. All of which are incorporated herein by reference for all purposes.

STATEMENT REGARDING FEDERALLY SPONSORED RESEARCH

This invention was made with government support under RO1GM38765, R01GM38765-2951, and P01GM095467 awarded by the National Institutes of Health. The government has certain rights in the invention.

BACKGROUND

The present disclosure relates generally to systems and methods for making medical or therapeutic decisions. More specifically, the present disclosure relates to using measurements taken during the time-course of clotting or coagulation of a patient's blood sample to make medical or therapeutic decisions.

Barrier breach poses multiple threats to human health in the form of bleeding, infection, and tissue destruction that is countered naturally by the processes of hemostasis, the acute inflammatory response, and tissue regeneration (1-3). Hemostasis ("stopping of blood") progresses rapidly through initiation of the extrinsic or intrinsic pathways that converge in coagulation and clot formation. These events are accompanied by inflammation through the activation of platelets, neutrophils, and monocytes within hemostatic plugs (4, 5). Specific arachidonic acid-derived eicosanoids play integral roles in hemostasis and inflammation, for example, thromboxane A2 (TxA2; see Table 1 for abbreviations of other lipid mediators) is a potent prothrombotic mediator, whereas prostaglandins and leukotrienes (6, 7) collectively increase vascular permeability, recruit neutrophils to injury sites, and position neutrophils for lipid mediator (LM) class switching from leukotriene biosynthesis to specialized pro-resolving mediators SPM production (8). This enables the production of specialized pro-resolving mediators (SPMs; see FIG. 4), a process that is pivotal for the transition from inflammation to resolution (8-11). SPMs, in turn, counter-regulate proinflammatory mediators (for example, cytokines and LM), accelerate efferocytosis (the phagocytosis of dying and dead cells) and wound healing, as well as reduce antibiotic requirements, in part, by enhancing phagocytosis without immune suppression (8, 12). Hence, SPMs are considered to be immunoresolvents because they are agonists of the resolution of inflammation and infections (13).

It would therefore be desirable to provide a method that exploits previously undiscovered interactions between SPMs generated during blood coagulation and immune responses.

SUMMARY

In one aspect, the present disclosure provides a method of providing a metabololipidomic profile and SPM signature on the progress of the innate host defense response following blood clotting comprising the steps of (a) taking one or more measurements in a patient's blood sample, wherein the sample is obtained during the time-course of clotting or coagulation or following clotting or coagulation, of pro-thrombotic and pro-inflammatory mediators (eicosanoids) and specialized pro-resolving mediators (SPMs), wherein a personalized metabololipidomic profile is obtained.

In other embodiments, the method additionally comprises the step of (b) comparing the measurement to that taken from normal or reference blood, thereby developing a comparison profile and using the profile to make a medical or therapeutic decision.

In some aspects, the clotting or coagulation is initiated by placing the sample in contact with a negatively charged surface and the sample is permeabilized by freeze-thaw to release the pro-thrombotic and pro-inflammatory mediators (eicosanoids) and the SPMs, wherein this permealization step occurs prior to the taking of the measurement.

In some aspects, the method of claim 6 wherein the released pro-thrombotic and pro-inflammatory mediators (eicosanoids) and the SPMs are purified prior to the taking of the measurement.

In some aspects, the released pro-thrombotic and pro-inflammatory mediators (eicosanoids) and the SPMs are purified by adding an agent to remove proteins and the released pro-thrombotic and pro-inflammatory mediators (eicosanoids) and the SPMs are purified by solid-phase extraction.

Typically, the metabololipodomic profile comprises an initial appearance of the eicosanoids $TxB_2$, $LTB_4$, and $PGD_2$ following clotting and the later appearance of a specific SPM-containing cluster. Typically, the specific SPM cluster comprises RvE1, RvD5, RvD1, MaR1 and $LXB_4$.

In one aspect, the method of claim 1 additionally comprising the step of removal of adenosine ex vivo, wherein the removal of adenosine occurs before taking the one or more measurements. In this aspect, the specific SPM cluster is enhanced in the metabololipodomic profile specific cluster and a second SPM cluster is unmasked and is represented in the profile. Typically, the second SPM cluster, unmasked by removal of adenosine, comprises RvD3, RvD4 and RvD6.

In another embodiment, the method provides a metabololipidomic profile and SPM signature on the progress of the innate host defense comprising the steps of (a) taking one or more measurements in a patient's sample, wherein the sample is a tissue or bodily fluid or excretion, of pro-thrombotic and pro-inflammatory mediators (eicosanoids) and specialized pro-resolving mediators (SPMs), wherein a personalized metabololipidomic profile is obtained.

DETAILED DESCRIPTION

In General

Figure 1:
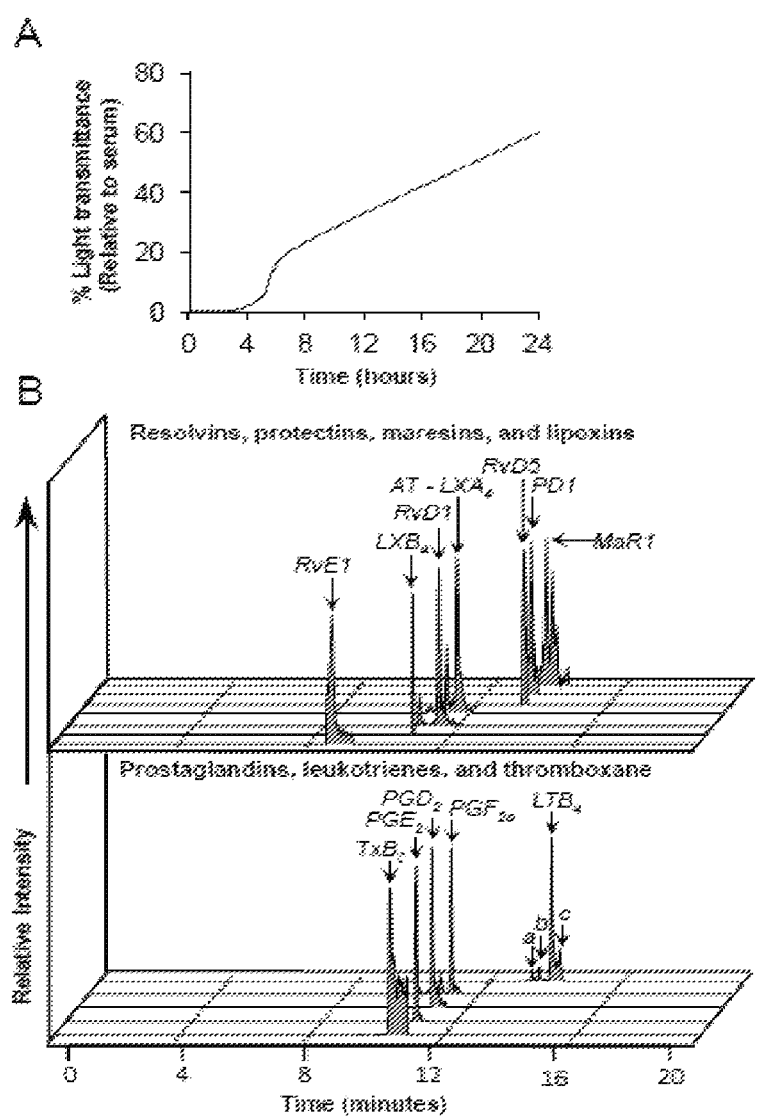
FIG. 1 illustrates that human blood coagulation initiates endogenous temporal production of SPMs and eicosanoids. (A to E) Freshly drawn human peripheral blood was incubated in silicone-coated tubes at 37° C. for the indicated times and coagulation was stopped by snap-freezing the samples for LC-MS/MS analysis (see Example 1, Materials and Methods). (A) Time course of the relative changes in the percentage light transmission at 750 nm in the blood samples during clot formation. (B) LC-MS/MS chromatograms of SPMs (top) and eicosanoids (bottom) that were identified in the samples. a=6-trans-$LTB_4$, b=6-trans,12-epi-$LTB_4$, and c=5S,12S-diHETE. (C) MS/MS spectra with diagnostic ions for the indicated identified mediators. Data in (A) to (C) are representative of 12 donors. (D) Concentrations of the indicated members of the SPM cluster and of eicosanoids in the blood samples over time. Data are means±SEM of 12 experiments. *P<0.05, P<0.01, *P<0.001, and ****P<0.0001 vs. the zero-hour time point by one-way ANOVA with Bonferroni Multiple Comparison Test. (E) Representative PCA score plot (top) and loading plot (bottom) showing temporal clustering of mediators from 12 individual donors. Gray denotes 0 hours; blue, 0.25 hours; red, 3 hours; and green, 24 hours after venipuncture and placement of blood in silicone-coated tubes without anticoagulants.
Figure 1:
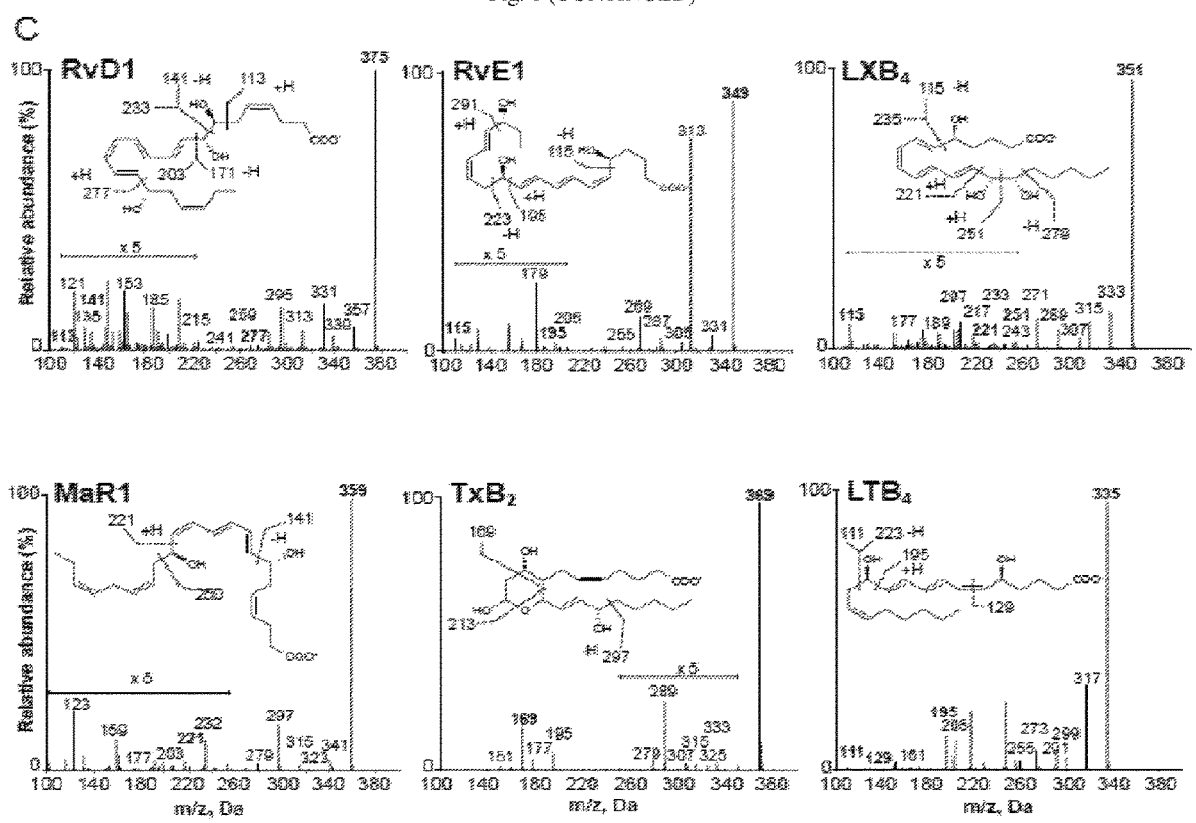
Figure 1:
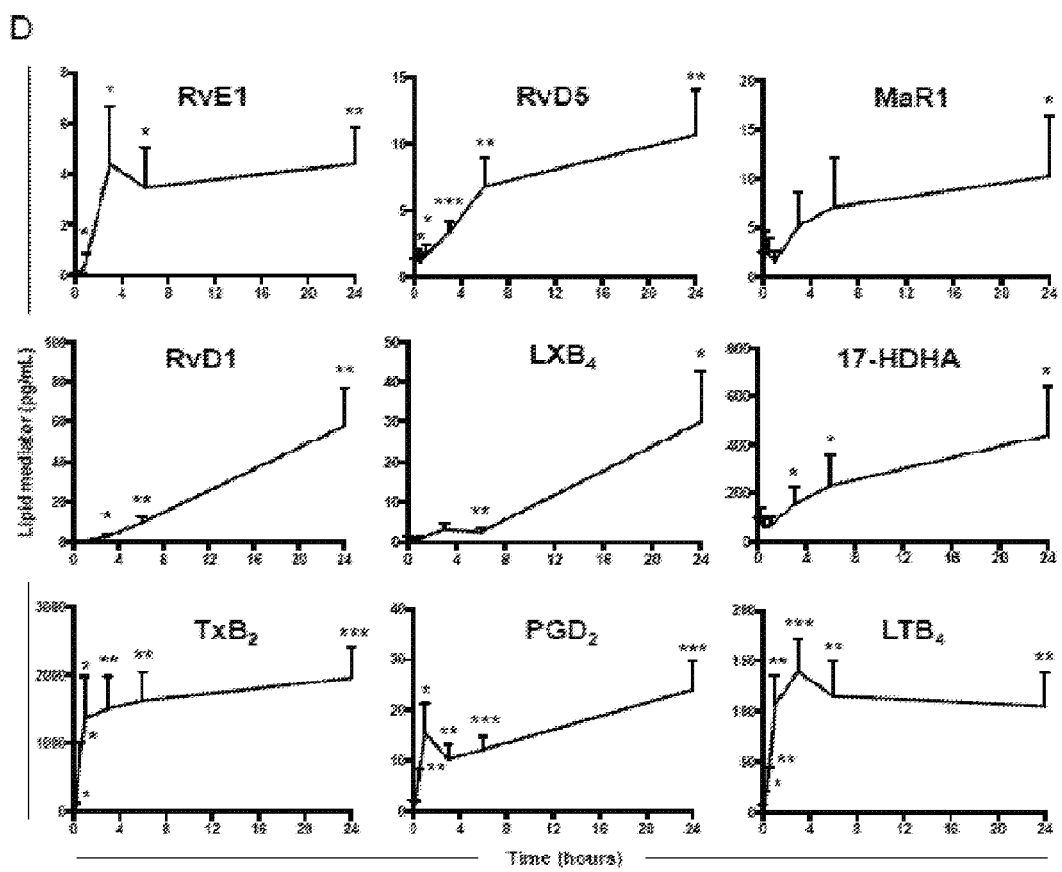
Figure 1:
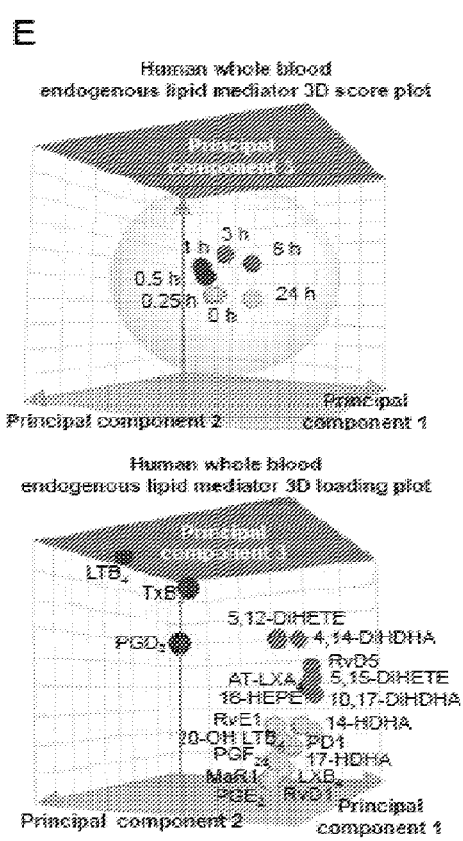

Disclosed herein is a method of providing a metabololipidomic profile and SPM signature on the progress of the innate host defense response.

By "metabololipidomic profile and SPM signature" we mean an examination and tabulation of an indicative group of pro-thrombotic and pro-inflammatory mediators and specialized pro-resolving mediators (SPMs) as described below in the Examples.

In one embodiment of the invention, the list of mediators is as listed in Table 4, which is a complete list of lipid mediators and pathway markers for identification and profiling of lipid mediator functional clusters and biosynthetic pathways. In other embodiments, one may wish to use fewer mediators in the panel/signature. For example, one may wish to examine at least 10, 15, or 20 mediators listed in Table 4. In another embodiment of the present invention, one may wish to include at least one or two members of each cluster described below.

Examination of the mediators will typically include examining the concentrations of the mediators over a time-course or relative to each other. One important element of the profile/signature is the emergence or lack of emergence of clusters relative to each other.

Lipid mediator panels of clusters are provided below:

Cluster A: Thromboxane $B_2$, Prostaglandin $D_2$, and Leukotriene $B_4$

Pro-inflammatory coagulation cluster of lipid mediators that increase in early phase of coagulation time-course. (For example, after addition of blood to negatively charged tubes, these mediators increase at 0.5 and 1 hour time points; see FIG. 1D and FIG. 1E).

Cluster B: Resolvin E1, resolvin D1, resolvin D5, maresin 1, lipoxin $B_4$

SPM coagulation cluster of lipid mediators that increase in late phase of coagulation time-course. (For example, after addition of blood to negatively charged tubes, these mediators increase at 3, 6, and 24 hour time points; see FIG. 1D and FIG. 1E).

Cluster C: Resolvin D3, resolvin D4, resolvin D6, AT-LXA$_4$, LXA$_5$, resolvin D1, resolvin E1, LXB$_4$.

This SPM cluster increases during late phase of coagulation time-course with the addition of 200 milliunits of human recombinant adenosine deaminase per 4 milliliters of human blood (see FIG. 2C-F and FIG. 7).

Cluster D: Thromboxane $B_2$, prostaglandin $E_2$, prostaglandin $D_2$, prostaglandin $F_{2\alpha}$, and leukotriene $B_4$.

This is a pro-inflammatory eicosanoid lipid mediator cluster. This cluster collectively promotes vascular permeability and neutrophil recruitment to sites of inflammation. This cluster is increased during the initiation of inflammation and can be used to assess the degree of a patient's inflammatory state.

Cluster E: RvD4, RvD5, and LTB$_4$.

Healthy tissue lipid mediator cluster. These mediators are increased in healthy tissue vs. diseased tissue.

Custer F: Thromboxane $B_2$ prostaglandin $D_2$

Diseased tissue lipid mediator cluster. These mediators are increased in diseased vs. healthy tissue.

In one embodiment, the method can include taking a measurement in a patient's blood sample, wherein the sample is obtained during the time-course of clotting or coagulation or following clotting or coagulation, of pro-thrombotic and pro-inflammatory mediators (eicosanoids) and specialized pro-resolving mediators SPM. Alternatively, the method can include taking a measurement in a patient's tissue, bodily excretion, or any other body fluid or part of a patient. From these measurements, a personalized metabololipidomic profile can be obtained.

The method may additionally comprise the step of comparing the measurement to that taken from normal or reference sample, for example a reference blood sample if the initial profile is taken from a blood sample, thereby developing a comparison profile. The method may additionally comprise the step of using the above profile to make a medical or therapeutic decision.

The method may additionally comprise the step of removal of adenosine ex vivo and the observation of a second SPM cluster. The adenosine may be removed, for example by incubation of the sample with adenosine deaminase. The adenosine deaminase is typically used at a concentration of 200 mU per 4 mls of whole blood. The second SPM cluster, unmasked by removal of adenosine, may comprise RvD3, RvD4 and RvD6.

In another aspect, the present disclosure provides a method of diagnosing a disease, illness, disorder, or health deficiency. The method comprises comparing a standard metabolipidomic profile obtained from normal or standard sample to a metabolipidomic profile obtained from a patient's sample, wherein diseased or pathologic sample can be identified by a difference in quantitative or temporal expression of the lipid mediators and pathway marker metabolites in the patient sample tissue compared with the lipid mediators and pathway marker metabolites in normal or standard sample. The medical or therapeutic decision may be an alternative assessment of health. For example, the profile may be used to make a diagnosis of cancer or determine if a patient's omega-3 fatty acid levels are within an acceptable range.

The diseased or pathologic sample may be associated with an event selected from the group of surgical events, infection, vascular inflammation, systemic inflammation, stroke, and cancer. As used herein, a diseased sample or pathologic sample can comprise any blood, tissue, excretion, or any other body part of a patient that is not in a state of good or normal health.

One may also wish to use the profile/signature of the present invention to determine the metabolic impact of drug treatment. For example, one may wish to example a patient sample before and after drug treatment in order to determine whether the drug is effective.

Patient Sample

The sample taken from the patient may be blood, tissue, an excretion, or any other body part or bodily fluid of a patient.

If the patient's blood sample is used to make the measurement, the blood may be whole blood. As used herein, whole blood is defined as blood drawn directly from the patient's body from which none of the components, such as plasma or platelets, have been removed. Alternatively, the measurements may be taken from a blood derivative, such as packed red blood cells, platelet concentrate, cryoprecipitate, plasma, or other such blood products.

The patient's blood sample may be treated prior to the measurements being taken. For example, the blood sample may be diluted, concentrated, or have an agent added to the sample. Certain components of the blood may be selectively removed prior to the measurements being taken.

If a blood sample is examined, one may wish to examine the patient sample at different time points during a clotting process and tabulate the appearance of factors comprising the profile/signature. If a blood sample, clotting or coagulation may be initiated by placing the sample in contact with a negatively charged surface, such as the heparin-covered tubes described in the Examples. The measurements may be taken during the time-course of clotting. For example, a measurement may be taken prior to the initiation of clotting as well as after periods of 0.1, 0.25, 0.5, 1, 2, 3, 4, 5, 6, 7, 8, 9, 10, 24, 48 hours, or any other comparable timeframe.

Prior to the measurement being taken, the sample may be permeabilized by freeze-thaw to release the pro-thrombotic and pro-inflammatory mediators (eicosanoids) and the SPMs. The Examples disclose one typical method of freeze-thaw. After undergoing freeze-thaw, the pro-inflammatory mediators (eicosanoids) and the SPMs may be further purified. The purification may include an agent may be added to the pro-thrombotic and pro-inflammatory mediators (eicosanoids) and the SPMs in order to remove unwanted proteins. The agent may be methanol. The purification may be achieved using solid phase extraction.

If tissue from the patient is being used to make the measurement, any tissue from the patient may be employed. As used herein, tissue is defined as any of the distinct types of material of which animals are made, consisting of specialized cells and their products. One may also wish to examine bodily fluids, such as urine or sweat. One may wish to examine waste or excretions products, such as feces. One may wish to examine breast milk.

Measurements

One must examine the patient samples for concentrations of the pro-thrombotic and pro-inflammatory mediators (eicosanoids) and specialized pro-resolving mediators SPM. The measurement may involve determining concentrations of specific eicosanoids or SPMs. These measurements may be taken using liquid chromatography, mass spectrometry, liquid chromatography tandem mass spectrometry, or other analytical techniques. The measurement may be specifically taken using via solid-phase extraction and lipid mediator-SPM liquid chromatography-tandem mass spectrometry.

Analysis of the Profile and Clinical Utility

The relationship between coagulation and the resolution of inflammation and infection by lipid mediators (LMs) through metabololipidomic-based profiling of human whole blood (WB) during coagulation can be used to identify temporal clusters of endogenously produced pro-thrombotic and proinflammatory LMs (eicosanoids), as well as specialized proresolving mediators. In addition to eicosanoids, a specific SPM cluster can be identified. The cluster may comprise resolvin E1 (RvE1), RvD1, RvD5, lipoxin B4, and maresin 1.

The metabololipodomic profile/signature may include concentrations of metabolites taken at various time points during the coagulation time-course of the blood sample or tissue. The metabololipodomic profile/signature may specifically comprise an initial appearance of the eicosanoids TxB2, LTB4, and PGD2 following clotting and the later appearance of a specific SPM-containing cluster. The specific SPM cluster may comprise RvE1, RvD5, RvD1, MaR1 and LXB4.

The profile may be compared to normal or reference values generated from previous results from other patients. These normal or reference values may be generic, or specific to age, sex, medical history, or any other specific medical determinant. The reference values and profiles generated therefrom may be coupled to specific diseases, illnesses, disorders, or health deficiencies. The reference values may alternatively be previously taken measurements of the specific patient in question. If the measurement is taken from a tissue sample, a reference tissue gathered from another location on the patient's body may be used.

One may wish to use the profile/signature of the present invention to aid in a medical or clinical diagnosis. When clinicians obtain the LM signature profile and combined with PCA cluster analysis of the quantities of SPM and other lipid mediators, typically measured by liquid chromatography separation and mass spectrometry measurement, one could expect prognostic cluster changes in the following scenarios according to our prophetic description:

a. Patients taking NSAIDs, e.g. indomethacin: clusters A and D will be decreased and cluster B and C will not decrease compared to subjects not taking NSAIDs (see FIG. 8A), thus giving a higher SPM vs. proinflammatory eicosanoid ratio. These changes yield a cluster ratio for pro-resolving mediators (SPM) vs. proinflammatory eicosanoids that positively correlates with resolution of inflammation and host defense (e.g., killing and removal of bacteria and microbes) that can also be applied to the additional scenarios below:

b. Patients taking COX-2 inhibitor drugs, e.g. celecoxib: clusters A and D will decrease and cluster B and C will not decrease compared to subjects not taking COX-2 inhibitor drugs. (see FIG. 8B)

c. Patients taking lipoxygenase inhibitors, e.g. zileuton, or corticosteroids: clusters A, B, C, and D will decrease compared to subjects not taking these inhibitors. (see FIG. 8B)

d. Patients with a fatty acid deficiency: clusters B and C will decrease compared to healthy subjects. Pro-resolving clusters will decrease compared to healthy subjects.

e. Patients taking omega-3 via supplements or nutrition: cluster B and C will increase compared to healthy subjects and/or fatty acid deficient subjects.
f. Patients with cancer: cluster E will decrease and cluster F will increase (see FIG. 11).
g. Patients taking blood thinners, e.g. the antiplatelet drug eptifibatide: cluster B and C will decrease (see FIG. 2b).
h. Patients taking anticoagulants, e.g. heparin: cluster A, B and C will decrease. (see FIG. 2a)
i. Patients that are immunocompromised: cluster B and C are expected to decrease.

Devices and Kits and Components for Sample Preparation and Metabololipidomics

Figure 10:
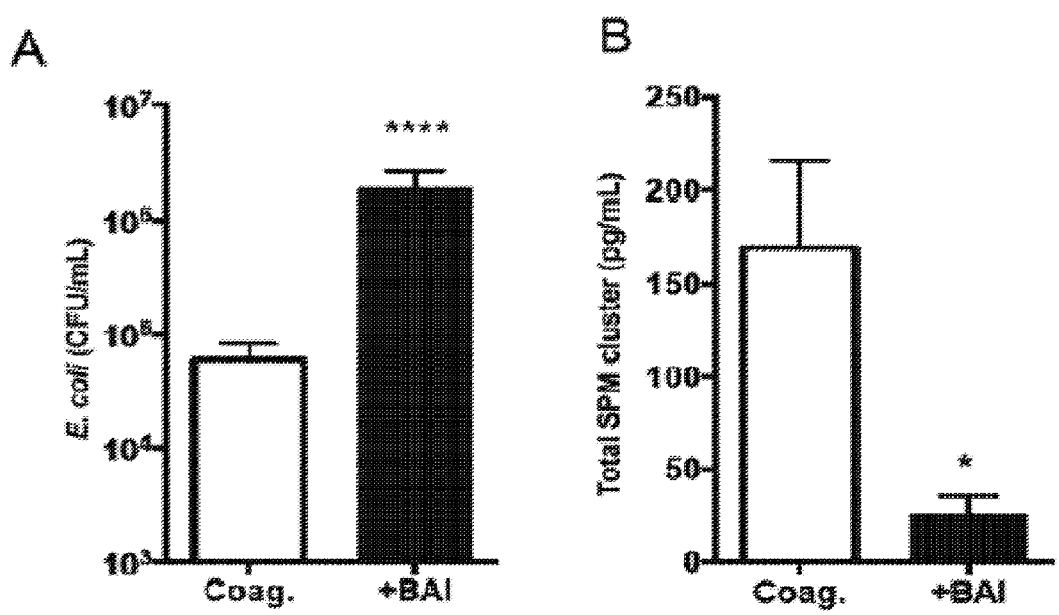
FIG. 10 illustrates the inhibitor of SPM formation BAI reduces bacterial killing. Freshly drawn human peripheral blood (4 mL) was placed in silicone-coated tubes at 37° C. for 24 h and was either stopped by snap freezing for LC-MS/MS, or supernatants were placed on LB agar plates and incubated overnight at 37° C. before enumeration of bacterial colonies. (A) Bacterial survival and (B) SPM in human peripheral blood (2.0 mL) incubated with $E.\ coli$ (7×108 CFU) in the presence or absence of a LOX inhibitor (BAI) 200 μM for 24 h; 37° C. (n=4 individual donors). Data are means±SEM; *P<0.05, ****P<0.0001 for +BAI vs. Coag using ratio t-test.

The method described herein can be used as part of a device or kit. Such a device or kit may include various solutions, compositions, separators, or other items that can be used to assist in taking the measurement of the patient's blood sample. For example, a typical kit of the present invention will comprise at least one, two, three or four of the following components:

a. Negatively charged surfaces with additional adenosine deaminase, such as silicone-coated, 10 mL tubes containing human recombinant adenosine deaminase (typically 200 milliunits/tube). Used for unmasking SPM-lipid mediator production and identification of SPM clusters.
b. Mixture of internal standards containing (d8-5-HETE, d5-RvD2, d5-LXA$_4$, d4-LTB$_4$, and d4-PGE$_2$; 500 pg/uL methanol). Used for lipid mediator quantitation.
c. Antibody detection analysis reagents specific to individual lipid mediator clusters (clusters A-F).
d. Antibody detection analysis reagents specific to resolvin D1, resolvin D2, resolvin D3, resolvin D4, resolvin D5, and resolvin D6.
e. Antibody detection analysis reagents specific to lipoxin A$_4$, lipoxin B$_4$, 15-epi-lipoxin A$_4$ (aspirin-triggered lipoxin A$_4$), and 15-epi-lipoxin B$_4$ (aspirin-triggered lipoxin B$_4$).
f. Antibody detection analysis reagents specific to protectin D1 and 17-epi-protectin D1 (aspirin-triggered protectin D1).
g. Antibody detection analysis reagents specific to maresin 1 and maresin 2.
h. Antibody detection analysis reagents specific to resolvin E1, resolvin E2, and resolvin E3.
i. Antibodies specific for lipid mediators described above (c-h) in a cartridge for capture and isolation of lipid mediators for liquid chromatography separation and quantitation by mass spectrometry as a diagnostic of inflammation, infection, and resolution of inflammation and to monitor fatty acid nutrition and supplementation.
j. Assay kit including antibody cartridges (described in i) for isolation of a patient's blood-derived SPMs and testing their functional bioactivity by measurement of phagocytosis and killing of bacteria in human whole blood. For example, patients with lower blood SPM levels (cluster B and C) vs. healthy subjects will have lower phagocytosis of bacteria by white blood cells in whole blood and higher numbers of live bacteria (i.e., reduced killing of bacteria) vs. healthy subjects. In blood taken from healthy subjects, addition of a lipoxygenase inhibitor reduces the level of cluster b and increases the number of live bacteria (see FIG. 10). Addition of SPMs to whole blood will increase phagocytosis and killing of bacteria in whole blood (see FIG. 3). These results can be used to inform clinicians of defects in a patient's host defense response and a way to test treatments that accelerate host defense and resolution of inflammation.

EXAMPLES

The following Examples are provided in order to demonstrate and further illustrate certain embodiments and aspects of the present invention and are not to be construed as limiting the scope of the invention.

Example 1

Results

LM-SPM Profiling of Human Blood Coagulation

To assess the relationship between blood coagulation, innate immune phagocytic function, and LMs, it was essential to obtain the complete LM profile by monitoring seven LM metabolomes focused on D-series resolvins, E-series resolvins, protectins, maresins, lipoxins, prostaglandins, and leukotrienes and their biosynthetic pathway markers during the coagulation time course of human blood. To this end, fresh human whole blood was subjected to coagulation through the intrinsic pathway (3) and monitored over time (0 to 24 hours) to confirm clot formation and its contraction. Each sample was rapidly snap-frozen and freeze-thawed (see Materials and Methods) to lyse the cells and extract total eicosanoids and SPMs from the supernatants for SPE-LC-MS/MS metabololipidomics. Blood clots formed between 8 to 15 min after the onset of coagulation, which was followed by clot retraction and serum formation, which increased rapidly between 4 and 8 hours based on increased 750-nm light transmission through the fluid phase that formed above retracted clots (FIG. 1A). The percentages of various leukocyte populations (neutrophils, lymphocytes, and monocytes) and their viability were determined throughout the time course (Tables 2 and 3).

Figure 5:
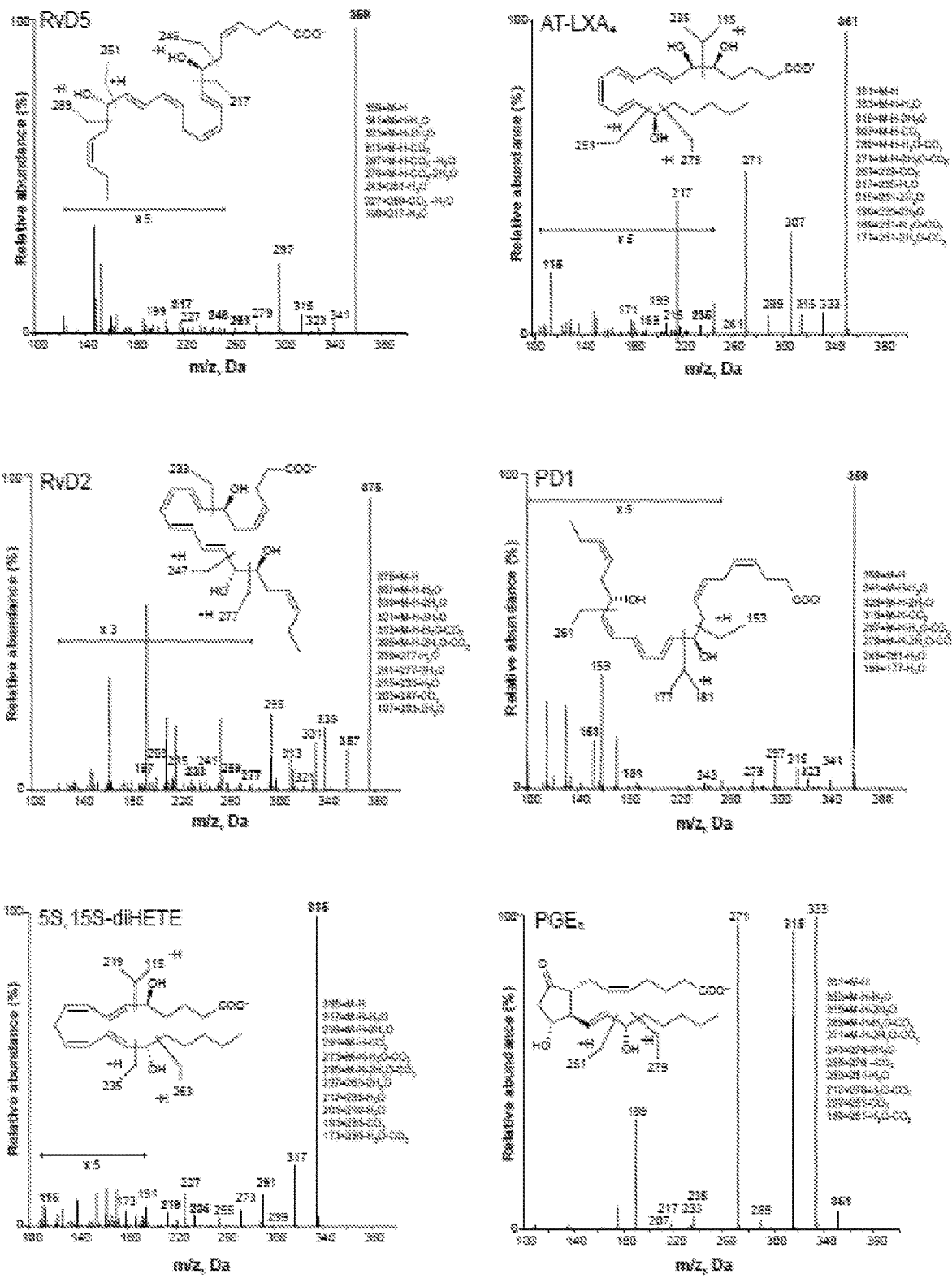
FIG. 5 illustrates LM identification in coagulated human peripheral blood. MS/MS fragmentation profiles of the indicated LMs. Results are from the same experiments shown in FIG. 1 panel C with these additional MS-MS for each LM identified.

Selective and sensitive targeted metabololipidomics identified increased endogenous amounts of both prothrombotic and proinflammatory mediators [thromboxanes (Txs), prostaglandin (PGs), and leukotriene (LTs)] and SPMs with different temporal profiles (FIG. 1, B to D, Table 4). LC-MS/MS-acquired results gave at least 6 diagnostic ions for each mediator identified together with matched LC retention times with authentic mediators (FIG. 1C and FIG. 5). The first cluster to appear included the eicosanoids TxB2 (a marker of TxA2), leukotriene B4 (LTB4), and PGD2 (FIG. 1D and Table 4). A select SPM cluster, consisting of RvE1, RvD1, RvD5, MaR1, and LXB4, increased throughout this time course, together with PGE2 and PGF2α. Note that although RvD2 was present in blood (FIG. 5), it was not apparently increased in abundance during coagulation. RvD2 is produced by human adipocytes (14) and other human tissues (15-17), prevents secondary thrombosis and necrosis in dermal burn wounds (18), and is protective in abdominal aortic aneurysm (19). Principal component analysis (PCA) confirmed that the production of TXB2, PGD2, and LTB4 were associated with early time points, whereas the specific SPM cluster was associated with later times during coagulation (FIG. 1E). Hence, initial platelet activation led to thromboxane production, as documented previously (20), and ongoing platelet-leukocyte interactions and transcellular biosynthesis contributed to the temporal production of SPMs during coagulation.

Regulation of Human SPM Production

Figure 6:
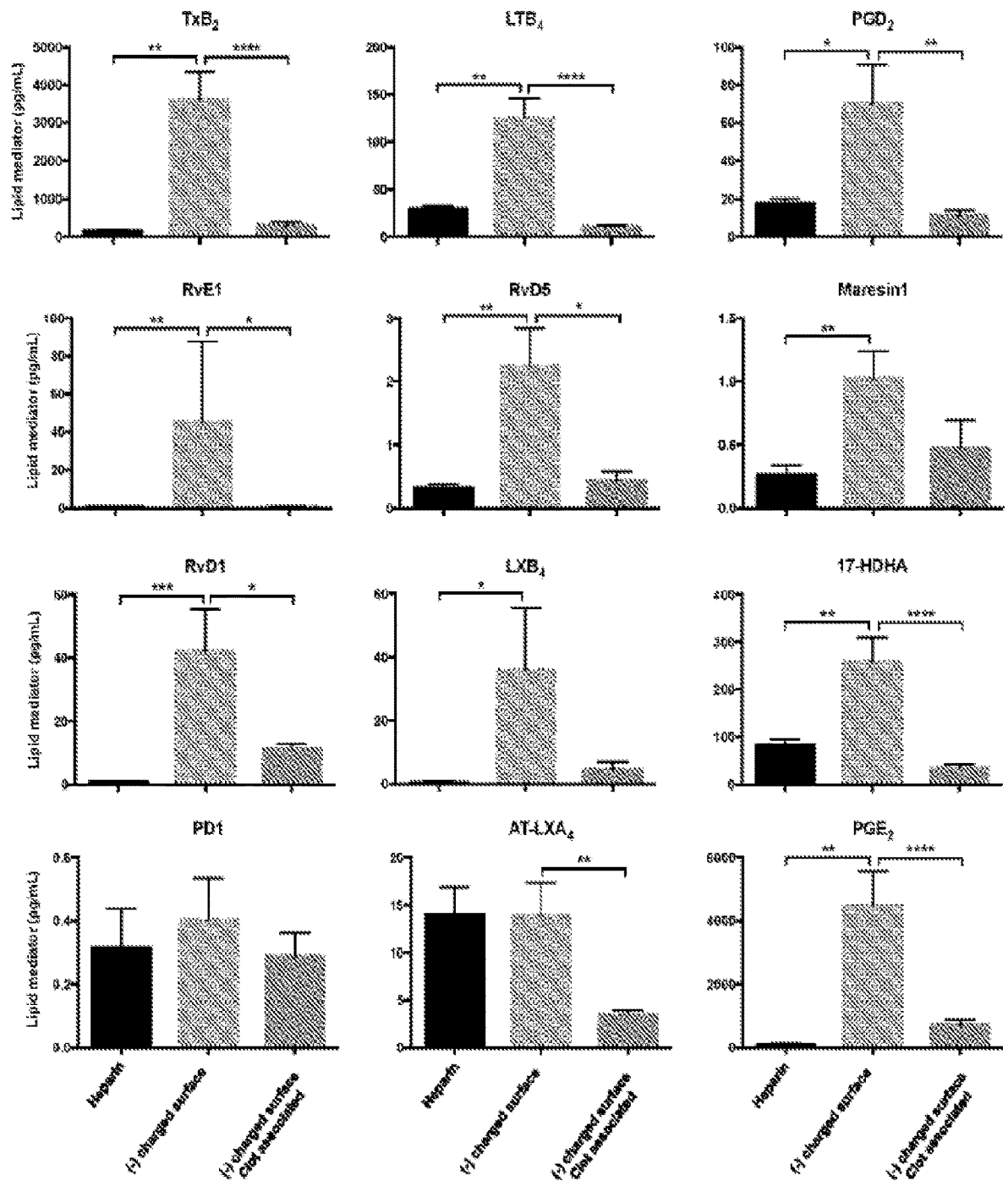
FIG. 6 illustrates coagulation leading to substantial increases in the production of SPMs, prostaglandins, and leukotrienes. Heparinized human blood was transferred to 15-ml polypropylene tubes (heparin 10 U/ml) and blood without heparin was transferred to silicone-coated tubes (-charged surface) before incubation at 37° C. for 24 hours. Samples were snap-frozen and centrifuged. Supernatants and pellets (clot-associated) were subjected to solid-phase extraction and LC-MS/MS LM metabololipidomics analysis as described in FIG. 1. Results are means±SEM of three individual donors. *P<0.05, P<0.01, *P<0.001, ****P<0.0001 by ratio t test.
Figure 7:
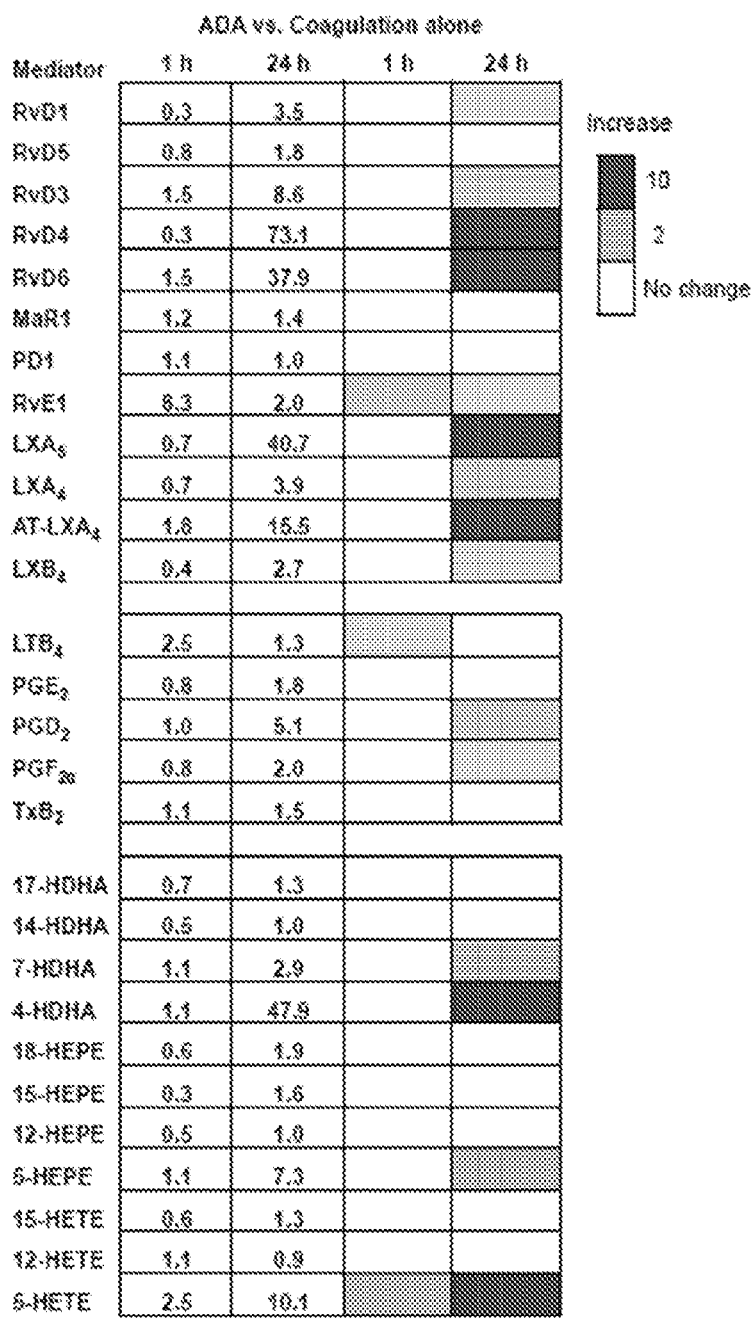
FIG. 7 illustrates the removal of adenosine enhancing SPM production and platelet-neutrophil interactions during coagulation. (A and B) Human peripheral blood was incubated with or without 200 mU of ADA during coagulation for 24 hours. Samples were then subjected to LC-MS/MS analysis of the indicated LMs (A) or to flow cytometric analysis of platelet-neutrophil aggregates (B). (A) Increases in bioactive lipid mediators and pathway markers in the presence of ADA vs. those in samples that underwent coagulation alone are expressed as average fold-changes from three individual donors. (B) Gating schematic for quantitation of platelet-neutrophil aggregates (CD42a+ CD16+) Data are representative of five individual donors and are from the same experiment shown in FIG. 2D.
Figure 7:
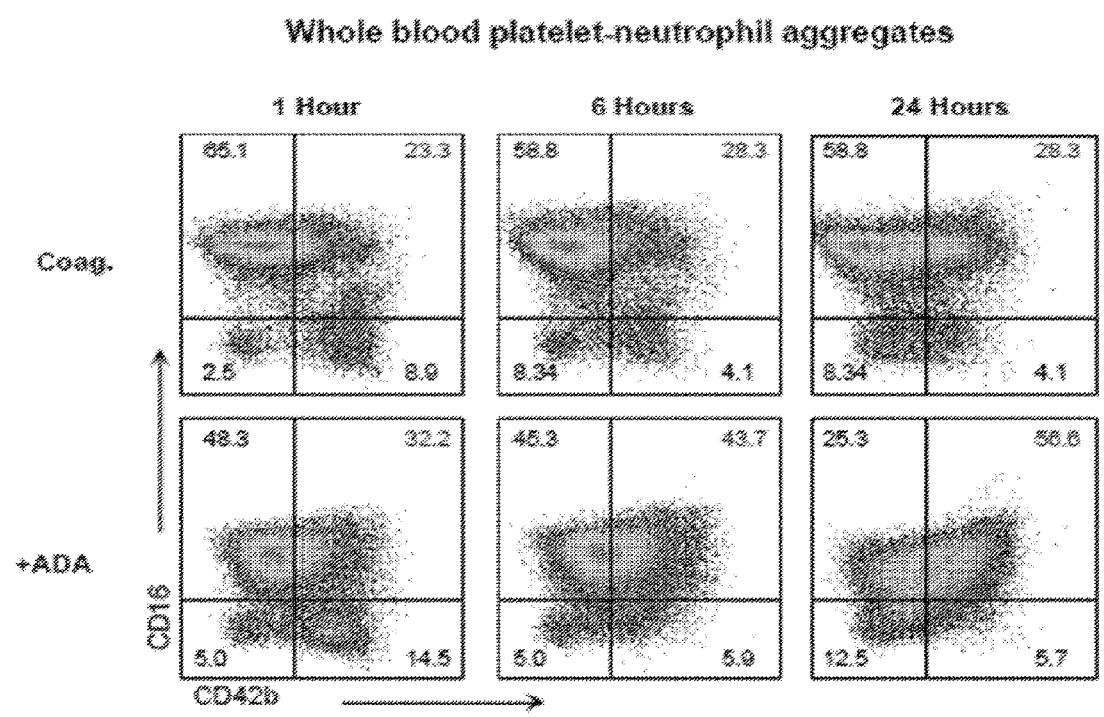

In healthy donors, the highest concentrations of SPMs generated within 24 hours of coagulation in blood were as follows: RvD1 (549 pM), LXB4 (303 pM), MaR1 (209 pM), RvD5 (115 pM), and RvE1 (58 pM) [the average values are reported (in pg/ml) in Table 4]. These SPMs were markedly reduced in concentration individually and in total 98% in blood containing the anticoagulant heparin (FIG. 2A and FIG. 6). The addition of an inhibitor of the platelet integrin αIIbβ3, a blocker of platelet-platelet interactions, reduced the total amount of the SPM cluster by ~50% (P<0.01) and concomitantly increased clot volume by ~20% (P<0.01) (FIG. 2B), without reducing cell viability (Table 5). These results suggest that clot formation and platelet integrin-mediated retraction of the clot were both required for SPM production, and that most SPMs were produced from endogenous cellular substrates in whole blood.

Unmasking of Further SPM Production and Specific SPM Pathways

Figure 2:
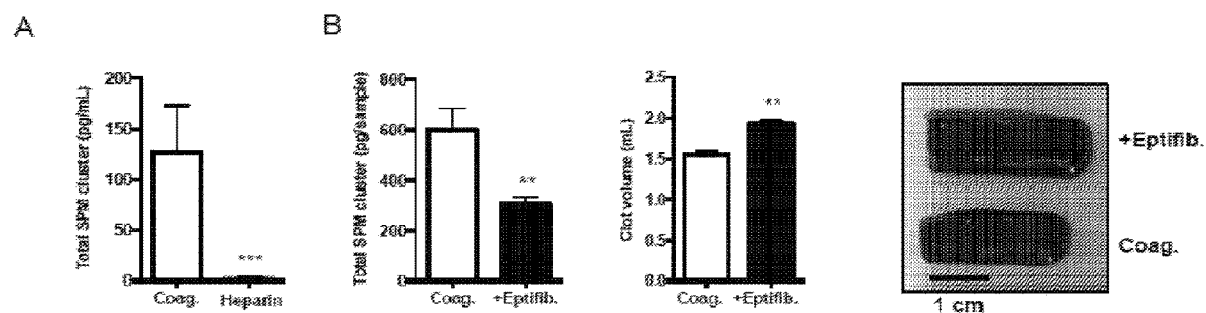
FIG. 2 illustrates regulators of SPM formation in human blood. (A to E) Freshly drawn human peripheral blood (4 ml) containing heparin (10 U/ml) was placed in polypropylene tubes (A) whereas human peripheral blood without anticoagulant was placed in silicone-coated tubes (B to E) and incubated at 37° C. for the time course of 0 to 24 hours (see Example 1, Materials and Methods). The samples were then subjected to snap-freezing for extraction and LC-MS/MS analysis. (A) Concentrations of the members of the SPM cluster (identified in FIG. 1) in samples treated without (Coag.) or with heparin (10 U/ml) during the incubation period. Data are means±SEM of three individual donors. (B) Left: Combined concentrations of the total SPM cluster, prostaglandins, and thromboxanes after 24 hours of coagulation in the presence or absence of the αIIbβ3 inhibitor eptifibatide (Eptifib.; 20 μM). Middle: Clot volumes after 24 hours of coagulation of the indicated samples. Right: Representative clot images. Data are means±SEM of three individual donors. (C) Concentrations of total SPMs and of the indicated individual SPMs after 24 hours of coagulation in the presence or absence of 200 mU ADA. Data are means±SEM of three individual donors. *P<0.05, P<0.01 by ratio t-test. (D) Top: LC-MS/MS measurements of adenosine concentrations in whole blood at the indicated time points during coagulation in the presence or absence of ADA. P<0.01 when compared to the zero-hour time point. Bottom: Flow cytometric analysis of the percentage of neutrophil-platelet aggregates, which were defined as being double-positive for CD16 and CD42b, in whole blood allowed to coagulate for the indicated times in the absence (Coag.) or presence of ADA. Data are means±SEM of five individual donors. *P<0.05, **P <0.01 by student's t test. For dot plots and gating, see FIG. 7B. (E) MS/MS fragmentation profiles with diagnostic ions for the indicated SPMs identified in (C). (F) Left: PCA score plot. Red denotes +ADA for 1 hour; yellow, coagulation for 1 hour; green, coagulation for 24 hours; blue, +ADA for 24 hours. Right: PCA loading plot showing temporal clustering of the indicated mediators from three individual donors. Red denotes LM at 1 hour; blue denotes 24 hours with ADA).
Figure 2:
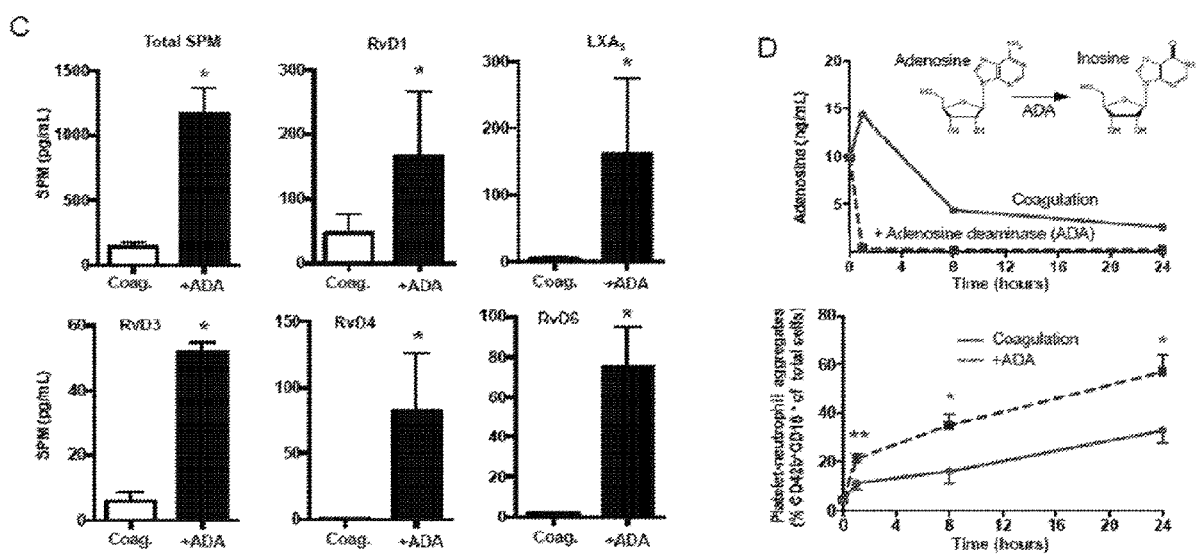
Figure 2:
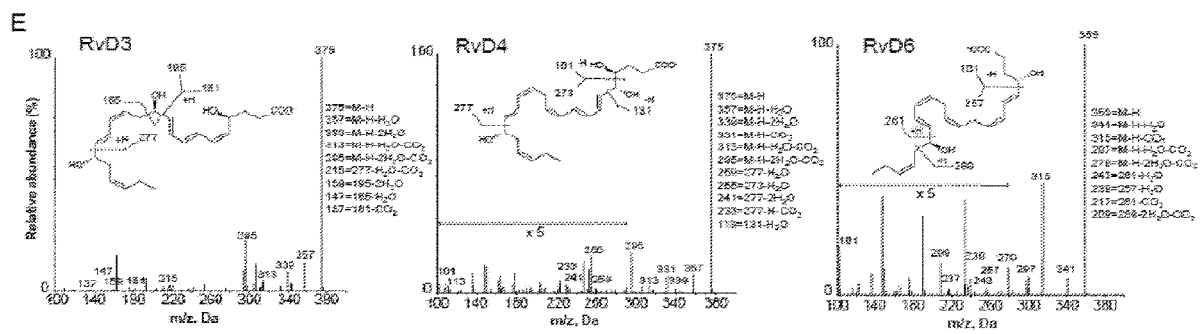
Figure 2:
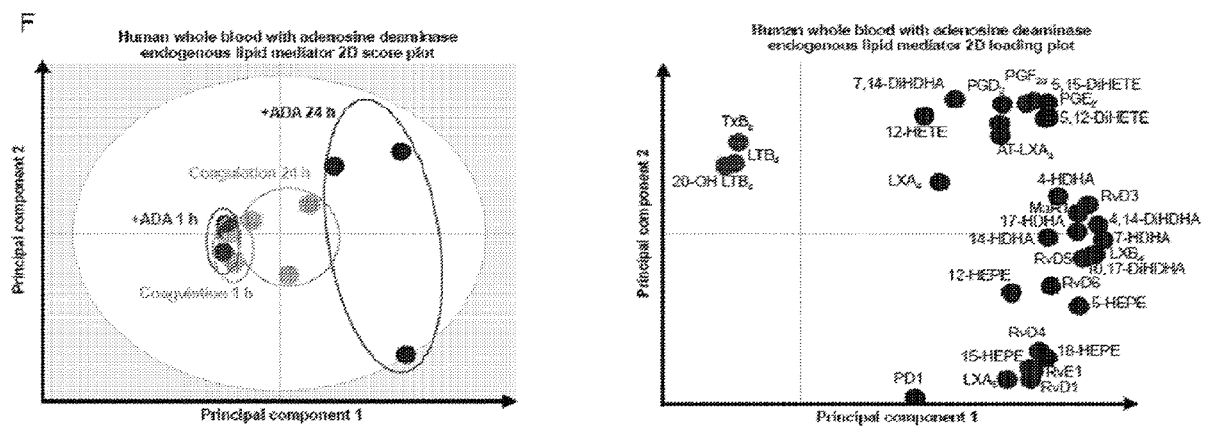

Because red blood cells release adenosine deaminase (ADA) to remove excess adenosine, we questioned whether this function affected SPM production during coagulation, and if so, whether removal of accumulated adenosine altered SPM production. Adenosine inhibits neutrophil functions, including the production of LTB4 (21). We found that ADA statistically significantly increased SPM production in blood (FIG. 2C), which in total was more than 8 times greater at 24 hours than that achieved by coagulation alone (FIG. 2C; see FIG. 7A for changes in the bioactive LM profile and pathway markers). Clearance of adenosine with ADA increased the production of specific SPMs from the coagulation cluster. These included RvD1 and RvD5, as well as the lipoxins, that is, LXA5 produced from EPA, and 15 epi-LXA4 produced from AA (FIGS. 2, C and D and FIG. 7A). RvD3, RvD4, and RvD6 were also identified and increased in abundance in the ADA-treated samples (FIGS. 2C and E). The greatest concentrations of these D-series resolvins were: RvD3 (150 pM), RvD4 (447 pM), and RvD6 (304 pM). ADA cleared adenosine (P<0.01) by 1 hour during coagulation based on the LC-MS/MS-based monitoring of the protonated adenine fragment; MRM transition 268>136 (FIG. 2D; see Materials and Methods). In addition, ADA statistically significantly increased the number of platelet-neutrophil aggregates during the time course of coagulation (FIG. 2D and FIG. 7B), suggesting that removal of adenosine enhanced SPM production through transcellular biosynthesis (22) involving platelet 12-LOX and neutrophil 5-LOX (23-25). In this context, platelet-neutrophil aggregates and transcellular biosynthesis lead to lipoxin production (23, 26) through LTA4, as well as maresin production through 14-HpDHA (24, 25). AT-LXA4 and LXA5 were also increased in abundance during coagulation (FIG. 2C and FIG. 7A). PCA indicated that the amounts of LTB4 (a potent chemoattractant) were greatest at 1 hour of coagulation (with and without ADA) and the SPMs were present in the greatest amounts at 24 hours of coagulation when ADA was added to clear adenosine (FIG. 2F). Cell viability was not decreased by ADA (Table 5). These results suggest that coagulation enables most SPM pathways in human blood to produce proresolving mediators that are substantially regulated by the local adenosine concentration and ADA.

Figure 8:
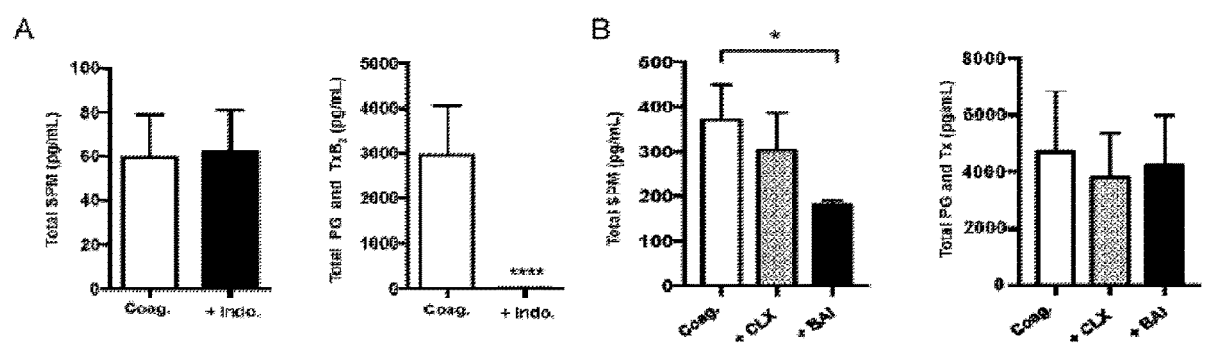
FIG. 8 illustrates SPM formation in human blood clots being regulated by lipoxygenase activity. (A and B) Freshly drawn human peripheral blood (4 ml) was placed in silicone-coated tubes at 37° C. for 24 hours and coagulation was stopped by snap-freezing before LC-MS/MS analysis was performed. Concentrations of total SPMs, prostaglandins, and thromboxanes after 24 hours of coagulation (Coag.) in the presence or absence of (A) 100 μM indomethacin (Indo.) (n=six individual donors), (B) 500 nM celecoxib (CLX) or 20 μM BAI (n=three individual donors). Data are means±SEM; *P<0.05 for +BAI vs. Coag; ****P<0.0001 for +Indo vs. Coag. using ratio t-test.

Next, we assessed the effects of therapeutic cyclooxygenase 1 (COX-1) and COX-2 inhibitors on SPM production during coagulation because NSAIDs block the biosynthesis of thromboxanes and prostaglandins, as well as increase bacterial killing in blood (27). We found that total prostaglandin and thromboxane production was blocked by indomethacin (>99% inhibition) compared to that during coagulation alone at 24 hours (FIG. 8A). In the presence of indomethacin, total SPM amounts did not substantially change compared to those in the absence of inhibitor (see Table 6 for the complete time course). Addition of the COX-2 inhibitor celecoxib did not statistically significantly alter the amounts of SPMs, prostaglandins, or thromboxanes in whole blood (FIG. 8B), whereas the addition of the lipoxygenase inhibitor baicalein (BAI), which has greater selectivity toward lipoxygenases than toward cyclooxygenases (28), reduced the total amounts of SPMs (FIG. 8B). Hence, these results suggest that the SPMs generated during coagulation were produced through lipoxygenase-initiated pathways and were not affected by NSAIDs.

Figure 9:
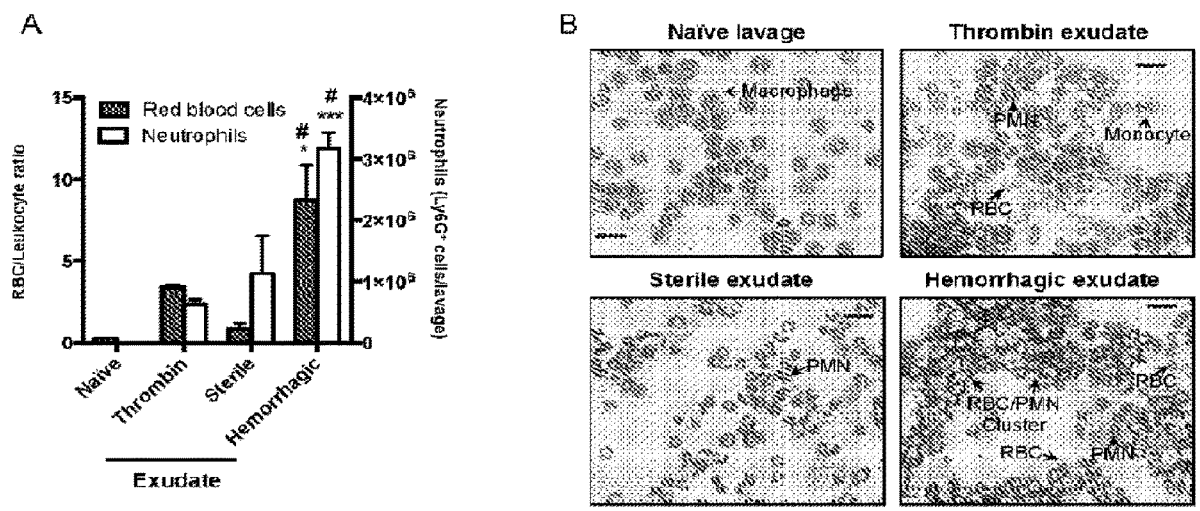
FIG. 9 illustrates coagulation increasing SPM production in hemorrhagic exudates. (A to D) Mice were given zymosan (1 mg/0.5 ml; sterile exudate), thrombin (5 U/0.5 ml; thrombin exudate), or a combination of both (hemorrhagic exudate) for 4 hours and then peritoneal exudates and naïve lavages were collected. (A) RBC vs. leukocyte ratios (blue bars; left axis) and neutrophil numbers (white bars; right axis) were determined using flow cytometry. (B) Leukocytes and RBCs from lavages were analyzed by light microscopy stained with Diff Quick a modified Wright Giemsa stain and are indicated by arrow heads. Scale bar, 20 μm. (C) The amounts of SPMs from the human blood coagulation cluster (C) and the amounts of eicosanoids (D) were determined. Data are means±SEM of three or four mice per condition. For hemorrhagic exudates vs. sterile exudates: $^{\#P<}$0.05, $^{\#\#}$P<0.01, $^{\#\#\#}$P<0.001; for hemorrhagic exudates vs. thrombin exudates: *P<0.05, P<0.01, *P<0.001 by two-tailed t test.
Figure 9:
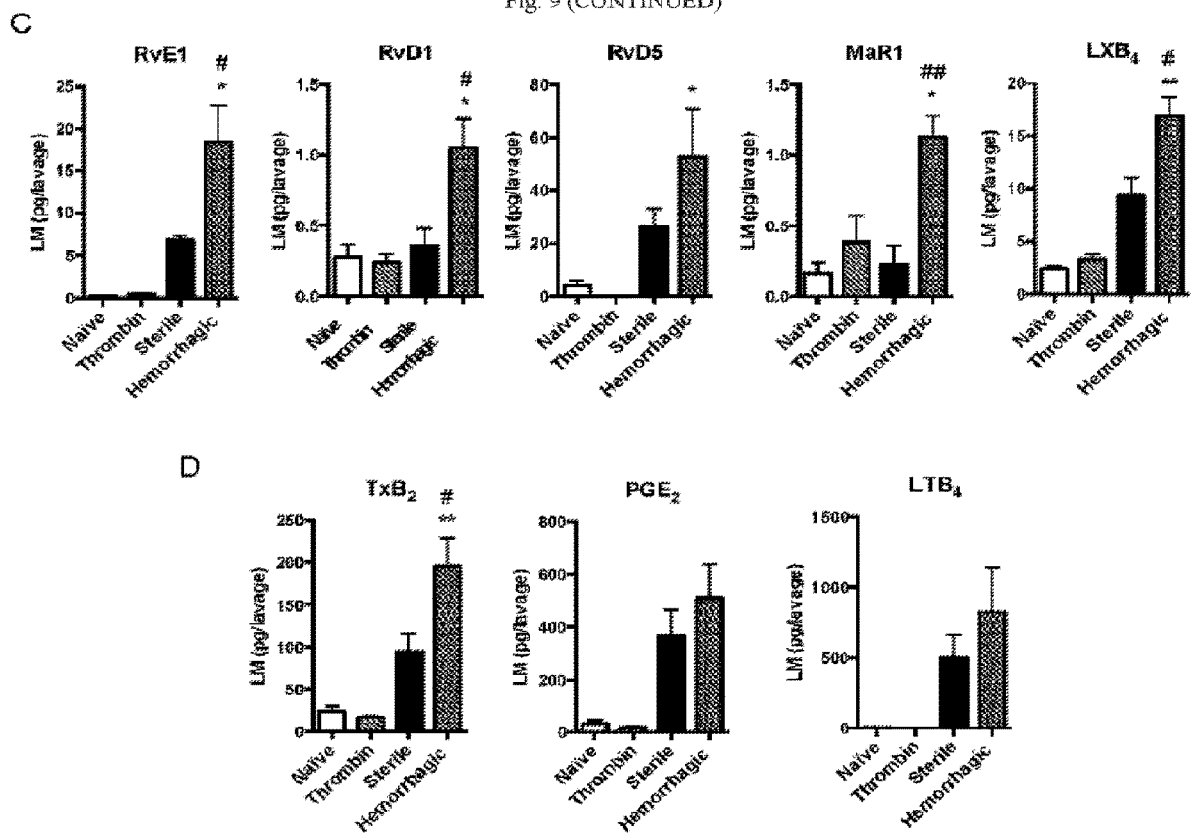

Excessive inflammation and vascular permeability promote the formation of hemorrhagic exudates that contain increased numbers of red blood cells and microthrombi (5), whereas sterile (29) and purulent exudates (30) contain predominantly leukocytes. To assess SPM production in vivo during coagulation, we used an established sterile zymosan-initiated murine peritonitis model (29) in combination with intraperitoneal (i.p.) administration of thrombin, which increased the numbers of red blood cells and leukocytes in hemorrhagic exudates (FIGS. 9, A and B). SPMs from the human blood coagulation cluster, namely RvE1, RvD1, RvD5, LXB4, and MaR1, were also present and statistically significantly increased in abundance in hemorrhagic exudates compared to sham saline alone (FIGS. 9, C and D). These results indicate that the same human SPM coagulation cluster that we identified in vitro was also produced in vivo in hemorrhagic exudates in mice.

SPM Host Defense Actions in Human Whole Blood and Phagocytes

Because RvE1, RvD1, RvD5, LXB4, and MaR1 each activated intracellular signaling in phagocytes (monocytes and neutrophils) within whole blood, we investigated the specific and combined host defense actions of these SPMs. Within human whole blood, this SPM panel (used together at 1 to 50 nM each) statistically significantly reduced *E. coli* survival obtained at concentrations as low as 1 nM (see FIG. 3A) and enhanced the phagocytosis of *E. coli* by neutrophils (CD66b+ cells) at concentrations as low as 100 pM (FIG. 3B). The SPM panel also enhanced the phagocytosis of *E. coli* by monocytes (CD14+ cells) in whole blood at 1 nM (p<0.01) as measured by flow cytometry.

We then assessed the effects of endogenous SPMs produced during coagulation on bacterial killing. Human blood was incubated with *E. coli* in the presence or absence of a lipoxygenase inhibitor. Bacterial counts were statistically significantly greater (>10-fold; P<0.0001) in the presence of the lipoxygenase inhibitor (FIG. 10A), which coincided with a >80% reduction in the abundances of members of this SPM cluster from coagulation (FIG. 10B). Thus, blockade of endogenous SPM production impaired bacterial killing by peripheral blood phagocytes.

Figure 11:
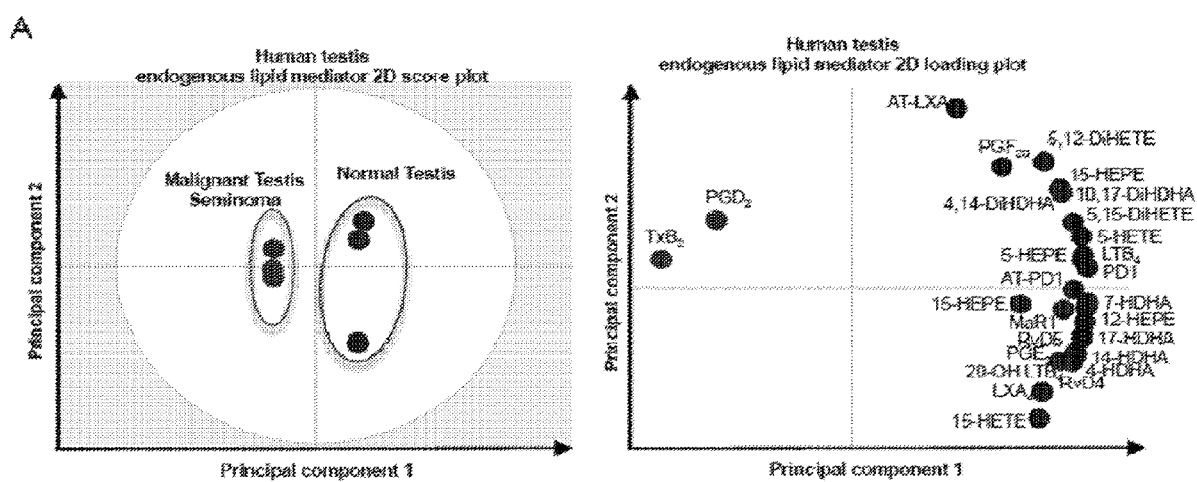
FIG. 11 illustrates LM profiles being distinct between normal and diseased human tissues. (A to C) Human testis tissue was profiled by LC-MS/MS. Patient demographics are as follows. Normal testis: 75 years old; Caucasian; deceased; history of metastatic melanoma (to lung and bone). Malignant testis: seminoma; 52 years old; Caucasian; living. (A) PCA score plot (left) and loading plot (right) showing clustering of LMs from three separate measurements. (B) Concentrations of total SPMs, LTB4, and total PG and TxB2 in the indicated samples. Data are means±SEM of three separate measurements. P<0.01, *P<0.001 by unpaired t test. (C) MS/MS fragmentation profiles of the indicated SPMs.
Figure 11:
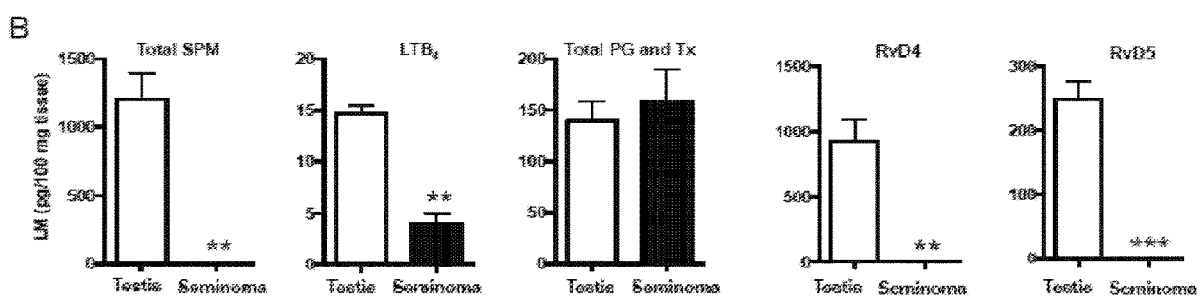

Thrombus formation compartmentalizes systemic bacteria within microvessels to minimize bacterial tissue invasion, which in part promotes the intravascular association between bacteria and macrophages (34). We therefore questioned whether clot-derived SPMs specifically enhanced the phagocytosis of bacteria by macrophages in addition to their clearance by blood neutrophils and monocytes. We found that the extent of phagocytosis of *E. coli* by human macrophages was statistically significantly enhanced by individual SPMs of the coagulation cluster, namely RvD1, RvE1, LXB4, and MaR1. Individually, LXB4 and RvE1 evoked the greatest increases in macrophage phagocytosis. Members of the SPM panel, each at 1 nM when used together, resulted in enhanced phagocytosis by macrophages when compared to that by macrophages treated with select SPMs alone (FIG. 3D). These results suggest that the SPMs produced during blood coagulation potently enhance bacterial killing and containment by the predominant leukocytes (that is, neutrophils and monocytes) in human blood. To further demonstrate the utility of this approach with diseased tissues versus healthy tissues, we obtained solid tissue tumors and healthy human testis, which is a known location for DHA enrichment in human organs, and malignant testis for direct comparisons. Each tissue gave clearly distinct LM-SPM profiles. For example, these tissues had both prostaglandins and thromboxanes, whereas healthy testis showed increased amounts of SPMs (FIG. 11). These data suggest that diseased and healthy tissues can be profiled and compared through our approach.

Discussion

Figure 3:
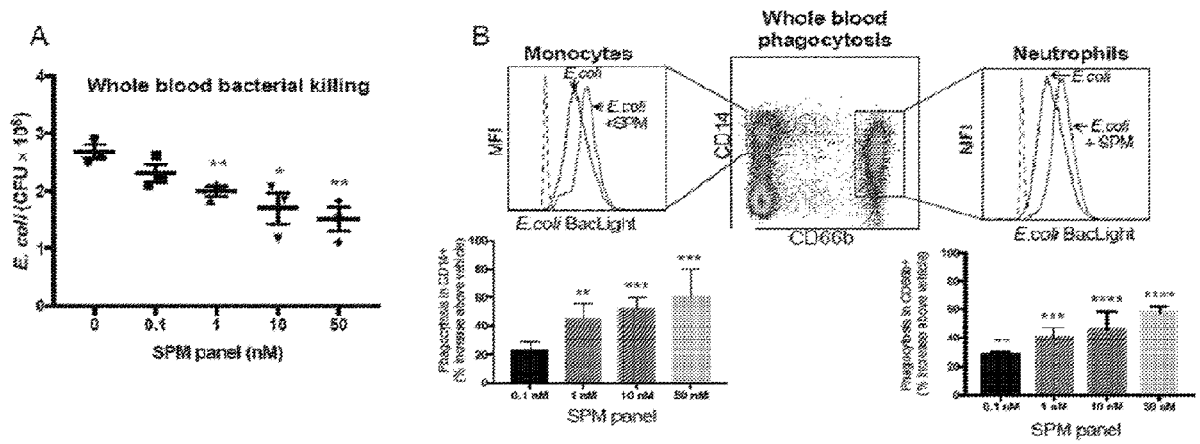
FIG. 3 illustrates SPMs produced during coagulation of whole blood enhance phagocytosis and bacterial killing. (A) Analysis of bacterial survival in human peripheral blood incubated for 15 min at 37° C. with RvE1, RvD1, RvD5, LXB4, and MaR1 (from the SPM panel) at the indicated concentrations or with vehicle control, which was followed by the addition of E. coli and further incubation for 60 min at 37° C. Data are means±SEM of three separate donors. *P<0.05, P<0.01 vs. vehicle by two-tailed t test. (B) Phagocytosis of BacLight Green-labeled E. coli by human peripheral blood neutrophils (CD66b+) and monocytes (CD14+) after incubation for 45 min at 37° C. in the absence or presence of members of the SPM panel [as described in (A)]. Top: The MFIs of the indicated cells were determined by flow cytometric analysis. Representative histograms are shown. Bottom: Data are means±SEM of four individual donors. P<0.01, *P<0.001, **P<0.0001 vs. vehicle control by one-way ANOVA with Bonferroni Multiple Comparison Test. (C) Real-time analysis of the phagocytosis of BacLight Green-labeled E. coli by human macrophages (incubated at a ratio of 50 bacteria per cell) after incubation for 15 min at 37° C. with vehicle or the indicated SPMs (1 nM each) separately or in combination (E. coli+SPM). Phagocytosis represented by MFI is presented as the mean of 4 fields (20λ) per condition (per well). Inset: Representative images from three separate donors. Scale bar, 50 μm. (D) Analysis of phagocytosis of E. coli at 180 min. Data are means±SEM of three separate donors. *P<0.05, **P<0.01 vs. SPM panel; ##P<0.01, ###P<0.001 vs. vehicle by one-way ANOVA with Bonferroni Multiple Comparison Test.
Figure 3:
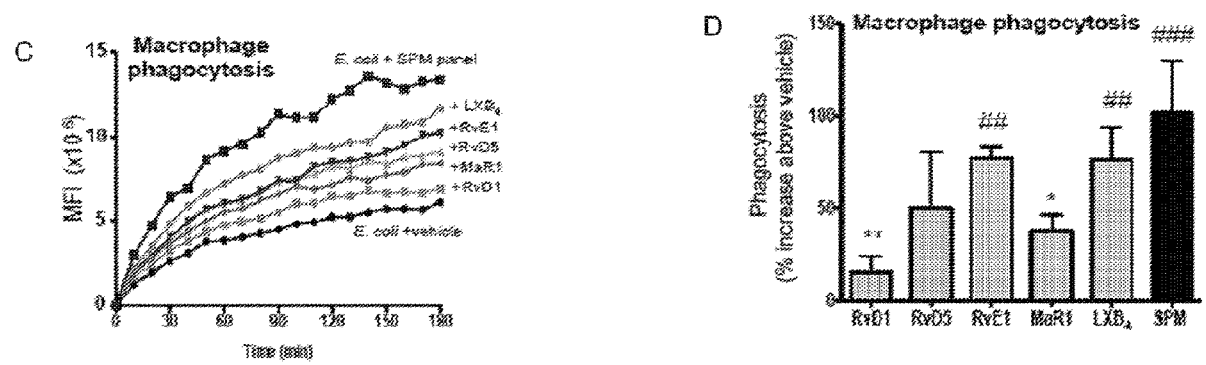
Figure 4:
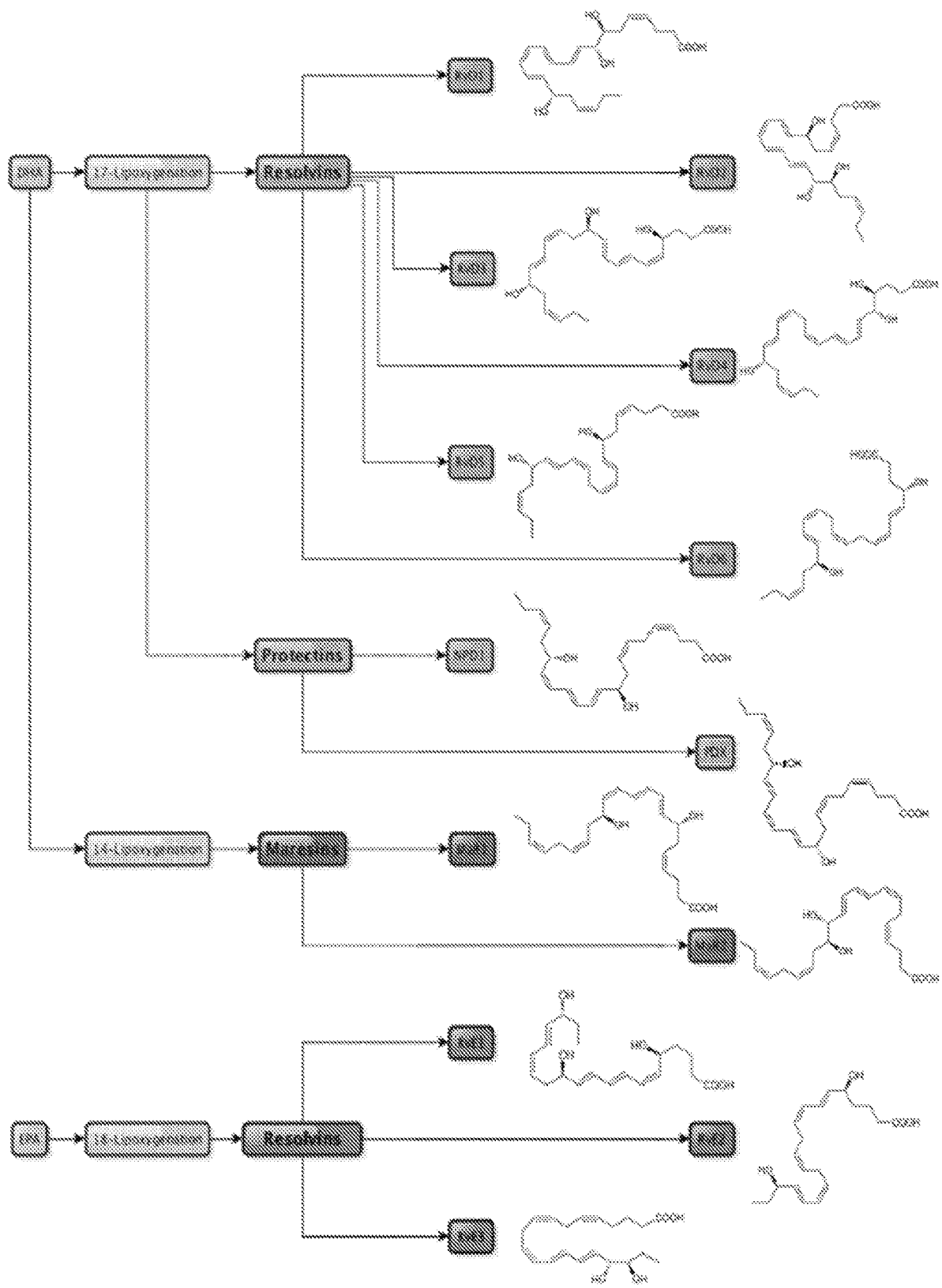
FIG. 4 illustrates SPMs and their biosynthetic pathways.

Thromboxanes and prostaglandins are well-established modulators of coagulation (6); however, the roles of lipoxygenase-derived mediators, such as the resolvins and other SPMs produced in human whole blood, are unclear. Our findings suggest that a specific cluster of SPMs is formed during coagulation and their actions target phagocytes in the surrounding milieu functioning in whole blood. RvE1 increases phagocytosis by isolated macrophages through GPCR-mediated pathways (that is, the ChemR23 receptor) that activate ribosomal S6 (32). RvD1 and MaR1 each increase the abundance of pCREB in human monocytes (35). Our single-cell analysis demonstrated that RvE1, RvD1, RvD5, LXB4, and MaR1 (constituents of the same clot-SPM cluster) each activated CREB and S6 in neutrophils and monocytes, which led to enhanced phagocytosis by these leukocytes in blood, accelerating the first line of defense against pathogens. Another SPM-activated pathway in human whole blood that we identified was the phosphorylation of S6 in B cells (FIGS. 3, C and D). This may play a role in B cell responses given that SPMs are also present in lymphoid organs (15), and that RvD1, RvD2 and MaR1 regulate the adaptive immune responses mediated by T cells (36). Of interest, supplementation of the diet with omega-3 fatty acids attenuates the production of proinflammatory cytokines (37) and increases the amounts of SPMs in peripheral blood (15, 38). A study identified that omega-3 essential fatty acids, the precursors of SPMs, were biomarkers of a lower risk for fatal coronary heart disease (39, 40). Hence, our results suggest a potential physiologic mechanism by which coagulation initiates the endogenous production of functional n-3-derived SPMs that affect innate immune cells. Because the physiologic coagulation of blood is protective in humans, SPM production by clots may be of direct relevance to pathophysiology events in surgery (41), infection (11, 27, 42, 43), vascular inflammation (44, 45), stroke, and cancer (46, 47).

Resolvins and protectin D1 are present in plasma and serum (15, 38). Specifically, RvD1, RvD2, PD1, and 17R-RvD1 were identified in human plasma (38) before it was possible to identify RvD4 with a matched synthetic standard (48). Thus, in view of the present results indicating that coagulation produces the SPM cluster (RvE1, RvD1, RvD5, LXB4, and MaR1), this did not appear to involve increases in the amounts of PD1, MaR2, RvD2, RvE2, or RvE3. Hence, the plasma SPM quantities and those of the specific members of the identified clot-driven SPM cluster may reflect blood-borne production of SPMs, the release of SPMs into circulation from tissues, or both. Although the SPMs identified herein were not studied under blood flow conditions, note that COX-2 is increased in both abundance and activity by laminar shear stress (49) and hypoxia (50). COX-2 can also contribute to the production of SPMs, including RvE1, by cell-cell interactions between blood leukocytes and vascular endothelial cells (8).

To illustrate and demonstrate the utility of our profiling system, we also determined whether differences in lipid mediator-SPM profiles between healthy and diseased tissues could be discerned with this LC-MS/MS-based metabololipidomic approach. As an example of this, healthy human testis tissue, which is rich in DHA that is essential for fertility and spermatogenesis (51), and malignant testis tissue each gave distinct profiles. The seminoma tissue had both prostaglandins and thromboxanes and the normal testis tissue had increased amounts of SPMs (FIG. 11). Normal testis tissue contained statistically significantly greater amounts of SPMs and LTB4 (FIG. 11B), illustrating the potential diagnostic capacity of our metabololipidomic approach with human whole blood and solid tissue tumors as well as suggesting a function for SPMs in this tissue.

Our LM-metabololipidomics results demonstrated a temporal sequence in the synthesis of the families of lipid mediators that was initiated through the coagulation of human blood. The prothrombotic TxA2 and the inflammatory eicosanoids (prostaglandins and leukotrienes) were rapidly produced by platelets, as anticipated, as well as by platelet-leukocyte aggregates, with a peak in the formation of specific proresolving mediators of inflammation. These resolution mediators included a distinct SPM cluster, consisting of RvD1, RvD5, RvE1, LXB4, and MaR1, each member of which activated distinct intracellular signaling pathways in single leukocytes within the whole blood matrix, involving ERK1/2, CREB, p38 MAPK, S6, and AKT. These SPMs produced through clot formation enhanced both the phagocytosis and killing of E. coli by human neutrophils, monocytes, and macrophages.

The full functional potential of the biosynthesized SPMs was obscured by the accumulation of local adenosine, which inhibited the production of SPMs. thus providing additional evidence for resolution-toxic agents that disrupt SPM production at sites of inflammation (8). Artifactual red cell hemolysis occasionally occurs during blood collection, which leads to an increase in the amount of adenosine, which reduces platelet-neutrophil interactions (52). Thus, clearing of adenosine increased platelet-neutrophil aggregation and the biosynthesis of RvD3, RvD4, and RvD6, which enabled quantitation of the full spectrum of D-series resolvins, except for RvD2, which was not increased during whole-blood coagulation (FIG. 1), yet is protective against abdominal aortic aneurysm (19) and secondary thrombosis and necrosis in thermal burn wounds (18). SPMs also stimulate macrophages to phagocytize thrombi in the form of fibrin clots (53), which may facilitate the remodeling of clots or their removal. The isolation and workup procedures reported herein could enable identification of the spectrum of SPMs produced by human tissue and their function in this milieu. Together, these results demonstrated previously uncharacterized links mediated by SPMs between the coagulation of blood and innate host defense mechanisms activated by specialized proresolving mediators in human tissues. This approach and new procedures for SPM profiling in human tissues opens new avenues for both personalized and precision medicine given that the substrates for LMs and SPMs are essential and are acquired by the host through nutrients.

Materials and Methods

Human Peripheral Blood Isolation

Fresh human blood was collected with or without heparin (10 units/ml) from healthy volunteers with specific tubes for collections and 19-gauge butterfly needles with collection syringes to minimize potential cell damage. Each volunteer gave informed consent under protocol #1999-P-001297, which was approved by the Partners Human Research Committee. All volunteers denied taking nonsteroidal anti-inflammatory drugs for ~2 weeks before donation.

Coagulation of Human Blood

Human whole blood was transferred in 4-ml aliquots to negatively charged, silicone-coated 10-ml tubes (BD) without anticoagulant. For experiments with heparin, the heparinized blood was placed in 15-ml polypropylene tubes before incubation at 37° C. For LM profiling at designated times, all samples were immediately subjected to a workup procedure by which whole blood was snap-frozen in a dry ice/isopropanol bath and were returned to room temperature (×3 cycles) before undergoing centrifugation at 100,000 g at 4° C. Supernatants (and clots for select experiments; see FIG. 6) were collected and were subjected to LC-MS/MS LM metabololipidomics.

LM Metabololipidomics

To obtain a complete blood profile of eicosanoids and SPMs each sample was subjected to a procedure involving snap-freezing of whole blood that was then thawed to room temperature three times and centrifuged at 100,000 g at 4°C for 30 min before undergoing solid-phase extraction (SPE). Internal standards including d8-5-HETE, d5-RvD2, d5-LXA4, d4-LTB4, and d4-PGE2 (500 pg each; Cayman Chemical) were added together with four volumes of methanol to facilitate protein precipitation. After centrifugation at 1000 g at 4° C. for 5 min, each sample volume was reduced using a stream of nitrogen gas to ≤10% methanol and next loaded onto solid-phase extraction (SPE) Isolute C18 SPE 3-mL, 100 mg cartridges (Biotage) after rapid acidification (<30 s) to ~pH 3.5. Before elution, LM bound to the SPE matrix were neutralized with ddH2O. Methyl formate fractions from the SPE were brought to dryness under a gentle stream of nitrogen and resuspended in 1:1 methanol:water before injection into a liquid chromatography-tandem mass spectrometry system consisting of a QTrap 5500 (AB Sciex) equipped with a Shimadzu LC-20AD HPLC (Tokyo, Japan). A Poroshell 120 EC-18 column (100 mm×4.6 mm×2.7 μm; Agilent Technologies) was kept in a column oven maintained at 50° C., and lipid mediators (LMs) were eluted in a gradient of methanol/water/acetic acid from 55:45:0.01 (v/v/v) to 100:0:0.01 at a flow rate of 0.5 ml/min. To monitor and quantify the amounts of lipid mediators of interest, multiple reaction monitoring (MRM) was used with MS/MS matching signature ion fragments for each molecule (at least six diagnostic ions; ~0.1 pg limits of detection as described previously (15)]. PCA was performed as described previously (15) with SIMCA software, version 13.0.3. Calibration curves were obtained daily from authentic (nonsynthetic) standards and matrix suppression for each targeted LM in snap-frozen blood, and supernatants determined and used for recovery and quantitation.

Adenosine Quantitation in Human Blood

Human blood was subjected to the same freeze-thaw procedure as was used for the metabololipidomics. After centrifugation at 1000 g at 4° C. for 5 min, supernatants were reconstituted with 4 volumes of methanol and kept on ice for 30 min to facilitate protein precipitation. Samples were then subjected to centrifugation at 1000 g at 4° C. for 5 min. Supernatants were reconstituted to <1% methanol and then taken to LC-MS/MS for identification and quantitation of adenosine by matched retention time with ≥99%, pure adenosine (Sigma) through MRM transition 268>136 for the protonated adenine fragment (54).

Flow Cytometric Analysis of Clots

Human peripheral blood was collected from healthy individuals without anticoagulant and allowed to coagulate for 24 hours as described earlier. Clots were washed with phosphate-buffered saline (PBS) containing Ca2+ (0.9 mM) and Mg2+ (0.5 mM) and then gently homogenized and passed through a 70-micron filter. Clot-derived cells were stained for flow cytometric analysis. Cells were stained in FACS buffer (PBS with 1% BSA and 0.1% sodium azide). Fc-receptor-mediated, nonspecific antibody binding was blocked by Human TruStain FcX solution, which was followed by incubation with APC-conjugated anti-human CD14 (clone HCD14), PercP-Cy5.5-conjugated anti-human CD20 (clone 2H7), PE-conjugated anti-human CD66b (clone G10F5), and APC Cy7-conjugated anti-human CD3 (clone HIT3a) (Biolegend). For viability assays, FITC-conjugated annexin V (BD) and propidium iodide (PI) were added to the cells according to the manufacturer's protocol. Samples were analyzed with a FACS Canto II flow cytometer (BD Bioscience) and FlowJo X Software.

Neutrophil-Platelet Interactions

Whole blood was collected from healthy individuals without anticoagulant and allowed to coagulate for 1, 6, or 24 h with or without ADA. Clots were washed with PBS and then gently homogenized and passed through a 70 micron-filter. Clot derived neutrophil-platelet interactions were analyzed by flow cytometry with FITC-conjugated anti-human CD16 antibody (clone ebio CB16), and PE-conjugated anti-human CD42b (clone HIP1). Neutrophils were identified by their cell surface expression of CD16 and high side and forward scatter. Platelets were identified based on their low side and forward scatter on a log scale and on their cell surface expression of CD42b. Neutrophil and platelet aggregates were identified as CD14-cells that were double-positive for CD42b and CD16 as CD14-,CD42b+,CD16+,SSChigh,FSChigh.

Murine Peritonitis and Hemorrhagic Exudates

All experimental procedures were approved by the Standing Committee on Animals of Brigham and Women's Hospital (protocol no. 2016N000145) and complied with institutional and US National Institutes of Health guidelines. Male FVB mice (6- to 8-weeks old) were given zymosan A (1 mg/0.5 ml; Sigma), thrombin (5 units/0.5 mL; Sigma), or both for 4 hours. Mice were then euthanized with isoflurane before peritoneal lavage was performed with 4.0 ml of ice-cold PBS without divalent cations. Lavages were subjected to LC-MS/MS for metabololipidomics analysis and flow cytometric analysis of neutrophil numbers with PE-conjugated anti-mouse Ly6G antibody (clone 1A8). Cells from the lavages were also attached to glass slides by cytospin, and the red blood cells and leukocytes were differentiated from each other with Wright Giemsa stain (Sigma) and enumerated in a minimum of four low-power fields per slide. The cells were also stained with Diff Quick (Electron Microscopy Science) according to the manufacturer's instructions to acquire images with a Keyence BZ-9000 (BIOREVO) inverted fluorescence phase-contrast microscope (40× objective) equipped with a monochrome/color switching camera using BZ-II Viewer software (Keyence).

Bacterial Killing in Human Whole Blood

*E. coli* (serotype O6:K2:H1) were cultured in LB broth and washed in sterile saline before being added to blood. Human peripheral blood (45 µl) was incubated with each member of the SPM panel (RvD1, RvD5, RvE1 MaR1, LXB4) at 0.1, 1, 10, or 50 nM or with vehicle control (5 µl of PBS, 0.1% ethanol) for 15 min at 37° C., which was followed by incubation with ~2×10$^7$ *E. coli* (5 µl) for 60 min at 37° C. Samples were then diluted 1:10$^5$ in PBS on ice and aliquots were placed on LB agar and incubated overnight in a 37° C. incubator. Colonies were enumerated by eye.

Whole Blood Bacterial Killing During Coagulation

Fresh human blood (2.0 ml) without anticoagulant was incubated with *E. coli* (~7×10$^8$) in the presence or absence of 200 µM baicalein (a LOX inhibitor; Sigma) and allowed to coagulate at 37° C. for 24 hours. Serum from blood were diluted in PBS on ice and aliquots were placed on LB agar and incubated overnight in a 37° C. incubator. Colonies were enumerated.

Phagocytosis with Human Peripheral Blood Phagocytes

Fresh heparinized whole blood (100 µl) was collected from healthy donors and incubated with a panel of SPMs (RvE1, RvD1, RvD5, LXB4, and MaR1; 0.1 to 50 nM each in combination) or vehicle control (0.1% ethanol) for 15 min at 37° C. *E. coli* was labeled with Baclight fluorescent Green dye (Life Technologies) according to the manufacturer's instructions. Labeled *E. coli* was added to samples at a phagocyte:bacterium ratio of 1:50 to initiate phagocytosis at 37° C for 45 min. Samples were then incubated with APC-conjugated anti-human CD66b antibody (to label neutrophils) and APC-Cy7-conjugated anti-human CD14 antibody (to label monocytes) (Biolegend) for 15 min on ice. Cells were washed twice with 2 ml of ice-cold PBS, which was followed by red blood cell lysis and fixation in 3% paraformaldehyde. Cells were then analyzed either with a BD FACS Canto II flow cytometer (BD Biosciences) or an ImageStream X imaging flow cytometer (Amnis). Fluorescence-associated phagocytes in the neutrophil (CD66b+) and monocyte (CD14+) populations were subsequently identified with FlowJo software version X.

Human Macrophages

Human peripheral blood mononuclear cells from deidentified healthy human volunteers from the Children's Hospital Boston blood bank were isolated by density-gradient, Ficoll-Histopaque isolation, which was followed by monocyte purification. The monocytes were then cultured for 7 days in RPMI 1640, 10% fetal calf serum (FCS) and were differentiated into macrophages through culturing with granulocyte-macrophage colony-stimulating factor (GM-CSF, 20 ng/ml).

Real-Time Analysis of Phagocytosis

Real-time imaging of human macrophages was performed by plating the cells (50,000 cells/well in PBS++) onto 8-well chamber slides. The chamber slides were kept in a Stage Top Incubation system for microscopes equipped with a built-in digital gas mixer and temperature regulator (TOKAI HIT model INUF-K14). A panel of SPMs (RvE1, RvD1, RvD5, LXB4, and MaR1; 1 nM each or in combination) was added to the macrophages for 15 min, which was followed by the addition of BacLight Green-labeled *E. coli* (at an *E. coli*: phagocyte ratio of 50:1). Images were then acquired every 10 min for 3 hours at 37° C with a Keyence BZ-9000 (BIOREVO) inverted fluorescence phase-contrast microscope (20× objective) equipped with a monochrome-color switching camera using BZ-II Viewer software (Keyence). Mean fluorescence intensity was quantified with a BZ-II Analyzer.

Statistical Analysis

Groups were compared by Student's two-tailed t-test (for two groups) or one-way ANOVA with Bonferroni Multiple Comparison Test (for more than two groups) with Prism software version 6 (GraphPad). The criterion for statistical significance was P<0.05. Principal component analysis (PCA) was performed with SIMCA 13.0.3 software (MKS Data Analytics Solutions).

TABLES

TABLE 1

Abbreviations of LMs and SPMs.

| Abbreviation | Definition |
|---|---|
| 5S,15S-diHETE | 5S,15S-dihydroxy-eicosa-6E, 8Z, 11Z, 13E-tetraenoic acid |
| AA | arachidonic acid |
| COX | cyclooxygenase |
| d deuterated | deuterated |
| DHA | docosahexaenoic acid |
| EPA | eicosapentaenoic acid |
| HDHA | hydroxy-docosahexaenoic acid |
| HEPE | hydroxy-eicosapentaenoic acid |
| HETE | hydroxy-eicosatetraenoic acid |
| HpETE | hydroperoxy-eicosatetraenoic acid |
| LC-MS-MS | liquid chromatography tandem mass spectrometry |
| LM | lipid mediators |
| LOX | lipoxygenase |
| LT | leukotriene |
| LTB$_4$ | leukotriene B$_4$, (5S, 12R-dihydroxy-eicosa-6Z, 8E, 10E, 14Z-tetraenoic acid) |
| LX | lipoxin |
| LXA$_4$ | lipoxin A$_4$ (5S, 6R, 15S-trihydroxy-eicosa-7E, 9E, 11Z, 13E-tetraenoic acid) |
| LXA$_5$ | lipoxin A$_5$ (5S, 6R, 15S-trihydroxy-eicosa-7E, 9E, 11Z, 13E, 17Z-pentaenoic acid) |
| LXB$_4$ | lipoxin B$_4$: (5S, 14R, 15S-trihydroxy-eicosa-6E, 8Z, 10E, 12E-tetraenoic acid) |
| MaR1 | maresin 1 (7R, 14S-dihydroxy-docosa-4Z, 8E, 10E, 12Z, 16Z, 19Z-hexaenoic acid) |
| MRM | multiple reaction monitoring |
| PCA | principal component analysis |
| PD | protectin |
| PD1 | protectin D1 (10R, 17S-dihydroxy-docosa-4Z, 7Z, 11E, 13E, 15Z, 19Z-hexaenoic acid), also known as neuroprotectin D1 (NPD1) |
| PGD$_2$ | 11-oxo-9α, 15S-dihydroxy-prosta-5Z, 13E-dien-1-oic acid |
| PGE$_2$ | 9-oxo-11α, 15S-dihydroxy-prosta-5Z, 13E-dien-1-oic acid |
| PGF$_{2α}$ | 9α, 11α, 15S-trihydroxy-prosta-5Z, 13E-dienoic acid |
| Rv | resolvin |
| RvD1 | Resolvin D1 (7S, 8R, 17S-trihydroxy-docosa-4Z, 9E, 11E, 13Z, 15E, 19Z-hexaenoic acid) |
| RvD2 | Resolvin D2 (7S, 16R, 17S-trihydroxy-docosa-4Z, 8E, 10Z, 12E, 14E, 19Z-hexaenoic acid) |
| RvD3 | Resolvin D3 (4S, 11R, 17S-trihydroxy-docosa-5Z, 7E, 9E, 13Z, 15E, 19Z-hexaenoic acid) |
| RvD5 | Resolvin D5 (7S, 17S-dihydroxy-docosa-4Z, 8E, 10Z, 13Z, 15E, 19Z-hexaenoic acid) |
| RvE1 | Resolvin E1 (5S, 12R, 18R-trihydroxy-eicosa-6Z, 8E, 10E, 14Z, 16E-pentaenoic acid) |
| RvE2 | Resolvin E2 (5S, 18R-dihydroxy-eicosa-6E, 8Z, 11Z, 14Z, 16E-pentaenoic acid) |
| RvE3 | Resolvin E3 (17R,18R-dihydroxy-eicosa-5Z, 8Z, 11Z, 13E, 15E-pentaenoic acid) |
| SPM | specialized pro-resolving mediator |
| SRM | standard reference materials |
| Tx | thromboxane |
| TxB$_2$ | 9α, 11, 15S-trihydroxy-thromba-5Z, 13E-dien-1-oic acid |

TABLE 2

Leukocyte and lymphocyte populations are consistent during coagulation. Cell populations from 5 separate experiments (n = 5) were each analyzed using flow cytometry (see above for cell type markers). Values are the mean +/− S.E.M.

| Clot time | Monocytes (%) | Neutrophils (%) | B cells (%) | T cells (%) |
|---|---|---|---|---|
| 0 hours | 3.6 ± 1.2 | 35.7 ± 6.0 | 6.6 ± 1.8 | 30.0 ± 3.7 |
| 1 hour | 3.2 ± 0.4 | 32.5 ± 7.6 | 2.0 ± 0.1 | 21.8 ± 1.0 |
| 6 hours | 3.6 ± 0.4 | 36.4 ± 2.5 | 2.8 ± 1.0 | 26.1 ± 3.1 |
| 24 hours | 2.1 ± 0.1 | 30.2 ± 3.4 | 2.1 ± 0.4 | 19.2 ± 2.7 |

TABLE 3

Leukocytes and lymphocytes remain viable during coagulation. Cell viabilities from 5 separate experiments (n = 5) were each analyzed using flow cytometry (see above for markers for apoptosis and necrosis). Values are the mean +/− S.E.M. Leukocytes and lymphocytes remain viable during coagulation+.

| Clot time | Live (%) | Necrotic (%) | Early apoptosis (%) | Late apoptosis (%) |
|---|---|---|---|---|
| 0 hours | 88.3 ± 1.0 | 0.8 ± 0.2 | 10.4 ± 0.7 | 1.5 ± 0.6 |
| 1 hour | 84.8 ± 1.7 | 1.0 ± 0.3 | 12.0 ± 1.9 | 2.2 ± 0.5 |
| 6 hours | 79.3 ± 2.2 | 1.3 ± 0.2 | 16.1 ± 1.6 | 3.9 ± 0.4 |
| 24 hours | 81.6 ± 2.5 | 0.8 ± 0.6 | 10.6 ± 1.2 | 6.4 ± 2.4 |

TABLE 4

LM concentrations in human whole blood during coagulation. LC-MS-MS-based LM metabololipidomics analysis was performed with human blood collected at 0, 0.25, 0.5, 1, 3, 6, and 24 hours after coagulation.

| Mediator | Coagulation t = 0 h Avg | SEM | Coagulation t = 0.25 h Avg | SEM | Coagulation t = 0.5 h Avg | SEM | Coagulation t = 1 h Avg | SEM |
|---|---|---|---|---|---|---|---|---|
| DHA metabolome | | | | | | | | |
| RvD1 | — | | — | | 0.4 ± | 0.2 | 0.5 ± | 0.3 |
| RvD2 | — | | — | | — | | — | |
| RvD3 | — | | — | | — | | — | |
| RvD4 | — | | — | | — | | — | |
| RvD5 | 0.8 ± | 0.6 | 1.3 ± | 0.8 | 1.1 ± | 0.7 | 1.7 ± | 0.8 |
| RvD6 | — | | — | | — | | — | |
| PD1 | 0.8 ± | 0.3 | 0.8 ± | 0.3 | 0.8 ± | 0.3 | 0.8 ± | 0.4 |
| 10S,17S-diHDHA | 1.3 ± | 0.6 | 1.1 ± | 0.5 | 0.8 ± | 0.4 | 1.0 ± | 0.4 |
| Maresin 1 | 1.4 ± | 1.2 | 2.9 ± | 1.9 | 2.4 ± | 1.6 | 1.6 ± | 1.1 |
| 7S,14S-diHDHA | 2.2 ± | 1.5 | 2.6 ± | 1.9 | 0.5 ± | 1.0 | 1.1 ± | 1.0 |
| 4S,14S-diHDHA | 44.1 ± | 32.6 | 25.4 ± | 16.7 | 15.2 ± | 8.9 | 14.3 ± | 8.7 |
| 17-HDHA | 61.2 ± | 37.5 | 84.5 ± | 56.1 | 59.6 ± | 35.3 | 65.2 ± | 38.4 |
| 14-HDHA | 893.1 ± | 335.8 | 1185.7 ± | 585.9 | 662.2 ± | 198.9 | 588.1 ± | 172.3 |
| 7-HDHA | 11.5 ± | 9.1 | 12.7 ± | 10.0 | 13.2 ± | 10.5 | 11.9 ± | 9.0 |
| 4-HDHA | 70.0 ± | 52.0 | 59.7 ± | 36.0 | 90.4 ± | 67.6 | 73.9 ± | 54.7 |
| DHA | 89076.1 ± | 36548.5 | 83199.7 ± | 18381.6 | 82468.1 ± | 21723.9 | 95770.8 ± | 28977.8 |
| EPA metabolome | | | | | | | | |
| RvE1 | — | | — | | — | | 0.4 ± | 0.2 |
| RvE2 | — | | — | | — | | — | |
| RvE3 | — | | — | | — | | — | |
| 18-HEPE | 204.5 ± | 83.8 | 314.4 ± | 148.2 | 236.9 ± | 96.4 | 244.5 ± | 74.0 |
| 15-HEPE | 134.8 ± | 58.1 | 214.3 ± | 107.2 | 167.8 ± | 79.5 | 187.7 ± | 74.9 |
| 12-HEPE | 4196.1 ± | 1697.7 | 4553.0 ± | 1639.4 | 4769.4 ± | 2060.5 | 4728.3 ± | 1201.7 |
| 5-HEPE | 20.7 ± | 11.6 | 24.1 ± | 12.4 | 19.3 ± | 9.6 | 22.6 ± | 9.1 |
| EPA | 15574.7 ± | 5999.8 | 14085.2 ± | 3519.9 | 14897.7 ± | 4567.2 | 16544.3 ± | 4585.4 |
| AA metabolome | | | | | | | | |
| $LXA_4$ | — | | — | | — | | — | |
| AT-$LX4_4$ | 3.6 ± | 1.5 | 6.5 ± | 3.0 | 6.1 ± | 3.6 | 8.1 ± | 5.4 |
| LXB4 | 1.1 ± | 0.8 | 1.0 ± | 0.4 | 0.9 ± | 0.4 | 1.6 ± | 0.6 |
| 5S,15S-diHETE | 2.2 ± | 0.9 | 2.4 ± | 1.0 | 2.0 ± | 0.8 | 3.6 ± | 1.4 |
| $LTB_4$ | 5.0 ± | 2.5 | 14.1 ± | 6.6 | 35.2 ± | 9.4 | 106.2 ± | 29.7 |
| 20-OH-$LTB_4$ | — | | 3.1 ± | 1.6 | 8.0 ± | 3.4 | 29.9 ± | 15.1 |
| 5S,12S-diHETE | 4.2 ± | 2.5 | 5.9 ± | 3.2 | 5.0 ± | 1.6 | 10.8 ± | 4.0 |

TABLE 4-continued

LM concentrations in human whole blood during coagulation. LC-MS-MS-based LM metabololipidomics analysis was performed with human blood collected at 0, 0.25, 0.5, 1, 3, 6, and 24 hours after coagulation.

| | | | | | | | | | |
|---|---|---|---|---|---|---|---|---|---|
| PGD$_2$ | 1.5 | ± | 0.6 | 1.6 | ± | 0.4 | 6.5 | ± | 1.8 | 15.6 | ± | 5.7 |
| PGE$_2$ | 2.2 | ± | 1.1 | 3.0 | ± | 0.8 | 22.1 | ± | 7.7 | 65.6 | ± | 17.3 |
| PGF$_{2a}$ | 1.1 | ± | 0.4 | 1.7 | ± | 0.4 | 7.4 | ± | 2.8 | 19.5 | ± | 8.9 |
| TXB$_2$ | 3.0 | ± | 1.1 | 87.2 | ± | 44.0 | 671.8 | ± | 344.4 | 1365.4 | ± | 614.8 |
| 15-HETE | 258.2 | ± | 142.4 | 303.0 | ± | 139.9 | 416.2 | ± | 133.8 | 1035.6 | ± | 408.1 |
| 12-HETE | 2238.8 | ± | 656.8 | 3515.2 | ± | 1009.8 | 4092.3 | ± | 999.5 | 6481.2 | ± | 1761.7 |
| 5-HETE | 487.6 | ± | 409.9 | 100.1 | ± | 49.4 | 103.2 | ± | 41.9 | 173.1 | ± | 65.6 |
| AA | 23726.9 | ± | 7439.9 | 25635.8 | ± | 5799.3 | 24374.6 | ± | 5033.5 | 30685.7 | ± | 7698.1 |

| | Coagulation t = 3 h | | Coagulation t = 6 h | | Coagulation t = 24 h | |
|---|---|---|---|---|---|---|
| Mediator | Avg | SEM | Avg | SEM | Avg | SEM |
| DHA metabolome | | | | | | |
| RvD1 | 3.0 ± | 1.1 | 9.6 ± | 3.1 | 57.8 ± | 18.9 |
| RvD2 | — | | — | | — | |
| RvD3 | — | | — | | — | |
| RvD4 | — | | — | | — | |
| RvD5 | 3.4 ± | 0.8 | 6.8 ± | 2.2 | 10.7 ± | 3.4 |
| RvD6 | — | | — | | — | |
| PD1 | 0.8 ± | 0.3 | 1.5 ± | 0.6 | 2.2 ± | 0.7 |
| 10S,17S-diHDHA | 2.4 ± | 0.7 | 4.1 ± | 1.1 | 7.9 ± | 1.6 |
| Maresin 1 | 5.2 ± | 3.4 | 7.1 ± | 5.1 | 10.3 ± | 6.1 |
| 7S,14S-diHDHA | 3.5 ± | 2.9 | 3.7 ± | 3.3 | 9.7 ± | 5.7 |
| 4S,14S-diHDHA | 32.9 ± | 14.0 | 60.2 ± | 31.6 | 111.6 ± | 55.8 |
| 17-HDHA | 152.7 ± | 72.8 | 230.8 ± | 126.8 | 439.7 ± | 203.3 |
| 14-HDHA | 2294.6 ± | 979.2 | 3295.5 ± | 1732.6 | 4038.9 ± | 1777.5 |
| 7-HDHA | 13.7 ± | 8.8 | 17.6 ± | 12.6 | 28.8 ± | 20.1 |
| 4-HDHA | 108.0 ± | 78.0 | 97.7 ± | 61.4 | 240.5 ± | 155.5 |
| DHA | 127830.5 ± | 35145.9 | 131952.1 ± | 36032.5 | 183397.3 ± | 52665.7 |
| EPA metabolome | | | | | | |
| RvE1 | 2.7 ± | 1.6 | 2.3 ± | 0.7 | 5.1 ± | 2.0 |
| RvE2 | — | | — | | — | |
| RvE3 | — | | — | | — | |
| 18-HEPE | 571.3 ± | 193.8 | 700.0 ± | 231.4 | 1321.6 ± | 360.7 |
| 15-HEPE | 620.7 ± | 248.4 | 863.0 ± | 359.2 | 1370.7 ± | 438.0 |
| 12-HEPE | 16844.3 ± | 4856.8 | 21319.3 ± | 5760.4 | 26591.1 ± | 6019.3 |
| 5-HEPE | 48.5 ± | 26.0 | 43.0 ± | 14.9 | 75.0 ± | 26.0 |
| EPA | 22451.5 ± | 6727.8 | 24004.8 ± | 5804.0 | 37232.5 ± | 9965.2 |
| AA metabolome | | | | | | |
| LXA$_4$ | — | | — | | — | |
| AT-LX4$_4$ | 11.9 ± | 7.0 | 16.3 ± | 9.9 | 22.5 ± | 12.4 |
| LXB4 | 3.8 ± | 1.4 | 3.0 ± | 0.9 | 29.6 ± | 12.7 |
| 5S,15S-diHETE | 5.1 ± | 1.4 | 9.7 ± | 2.6 | 20.2 ± | 6.2 |
| LTB$_4$ | 139.9 ± | 32.5 | 115.4 ± | 35.0 | 105.2 ± | 33.3 |
| 20-OH-LTB$_4$ | 51.3 ± | 20.7 | 66.5 ± | 29.3 | 47.0 ± | 16.2 |
| 5S,12S-diHETE | 29.2 ± | 11.7 | 36.7 ± | 13.8 | 39.5 ± | 12.5 |
| PGD$_2$ | 10.3 ± | 2.9 | 12.2 ± | 2.6 | 24.1 ± | 5.5 |
| PGE$_2$ | 83.8 ± | 19.2 | 108.1 ± | 25.3 | 1286.8 ± | 255.5 |
| PGF$_{2a}$ | 31.6 ± | 11.3 | 44.1 ± | 11.8 | 168.4 ± | 43.1 |
| TXB$_2$ | 1509.6 ± | 472.4 | 1625.6 ± | 432.5 | 1959.6 ± | 446.0 |
| 15-HETE | 2220.3 ± | 820.6 | 3099.5 ± | 1395.7 | 4015.6 ± | 1146.7 |
| 12-HETE | 14018.7 ± | 3723.6 | 15921.7 ± | 6484.5 | 16532.4 ± | 4721.9 |
| 5-HETE | 258.5 ± | 82.7 | 282.1 ± | 104.2 | 436.6 ± | 161.2 |
| AA | 41191.8 ± | 8545.7 | 39809.1 ± | 8886.5 | 46263.5 ± | 11293.6 |

LM concentrations (pg/ml) are expressed as means ± SEM of 12 donors.

(—) denotes concentrations < 0.1 pg/ml.

TABLE 5

Leukocytes and lymphocytes are viable in the presence of eptifibatide or ADA during coagulation. Cell viability n = 3; analyzed using flow cytometry (see methods for markers for apoptosis and necrosis). Values are the mean +/− S.E.M.

| Treatment | Live (%) | Necrotic (%) | Early apoptosis (%) | Late apoptosis (%) |
|---|---|---|---|---|
| Vehicle | 86.5 ± 2.3 | 1.4 ± 0.5 | 8.0 ± 1.8 | 4.0 ± 0.6 |
| +Eptifibatide | 90.6 ± 1.3 | 0.9 ± 0.1 | 5.1 ± 1.9 | 2.0 ± 0.5 |
| +ADA | 81.5 ± 0.5 | 2.7 ± 2.0 | 9.9 ± 2.9 | 5.8 ± 1.4 |

TABLE 6

LM concentrations in human whole blood during coagulation in the presence of indomethacin. LC-MS-MS-based LM metabololipidomics analysis was performed with human blood collected at 0, 0.25, 0.5, 1, 3, 6, and 24 hours after coagulation in the presence of indomethacin. LM concentrations (pg/ml) are expressed as means ± SEM of six donors. (—) denotes concentrations <0.1 pg/ml.

| Mediator | Indomethacin t = 0 h Avg | SEM | Indomethacin t = 0.25 h Avg | SEM | Indomethacin t = 0.5 h Avg | SEM | Indomethacin t = 1 h Avg | SEM |
|---|---|---|---|---|---|---|---|---|
| DHA metabolome | | | | | | | | |
| RvD1 | — | | 0.4 ± | 0.3 | 0.5 ± | 0.3 | 0.6 ± | 0.4 |
| RvD2 | — | | — | | — | | — | |
| RvD3 | — | | — | | — | | — | |
| RvD4 | — | | — | | — | | — | |
| RvD5 | 1.2 ± | 0.8 | 1.6 ± | 1.1 | 2.1 ± | 1.5 | 2.6 ± | 1.7 |
| RvD6 | — | | — | | — | | — | |
| PD1 | 0.5 ± | 0.3 | 0.5 ± | 0.2 | 0.6 ± | 0.3 | 0.9 ± | 0.5 |
| 10S,17S-diHDHA | 0.3 ± | 0.2 | 0.4 ± | 0.3 | 0.4 ± | 0.2 | 0.4 ± | 0.3 |
| Maresin 1 | 1.0 ± | 0.8 | 1.9 ± | 1.6 | 0.4 ± | 0.2 | 0.6 ± | 0.5 |
| 7S,14S-diHDHA | 0.7 ± | 0.8 | — | | — | | 0.2 ± | 0.6 |
| 4S,14S-diHDHA | 2.8 ± | 1.5 | 3.2 ± | 1.9 | 3.0 ± | 1.6 | 2.5 ± | 1.5 |
| 17-HDHA | 16.2 ± | 8.7 | 18.9 ± | 8.5 | 19.7 ± | 8.0 | 25.5 ± | 10.6 |
| 14-HDHA | 485.7 ± | 259.3 | 491.0 ± | 202.0 | 436.3 ± | 160.1 | 430.6 ± | 156.7 |
| 7-HDHA | 1.4 ± | 0.6 | 1.6 ± | 0.6 | 1.9 ± | 0.7 | 2.1 ± | 0.4 |
| 4-HDHA | 8.5 ± | 4.1 | 10.7 ± | 4.9 | 11.3 ± | 3.5 | 11.8 ± | 3.2 |
| DHA | 28879.8 ± | 12073.0 | 49377.8 ± | 20997.4 | 57569.2 ± | 22040.3 | 54291.5 ± | 19253.8 |
| EPA metabolome | | | | | | | | |
| RvE1 | — | | — | | — | | — | |
| RvE2 | — | | — | | — | | — | |
| RvE3 | — | | — | | — | | — | |
| 18-HEPE | 39.8 ± | 14.2 | 64.4 ± | 23.0 | 85.1 ± | 35.6 | 103.7 ± | 22.4 |
| 15-HEPE | 25.2 ± | 11.2 | 37.2 ± | 16.4 | 44.9 ± | 19.5 | 55.9 ± | 18.4 |
| 12-HEPE | 1380.0 ± | 692.1 | 1964.3 ± | 963.5 | 2794.9 ± | 1334.6 | 3115.6 ± | 1233.5 |
| 5-HEPE | 2.5 ± | 0.8 | 3.7 ± | 1.2 | 6.6 ± | 2.3 | 7.7 ± | 1.3 |
| EPA | 3238.1 ± | 830.0 | 4830.2 ± | 1283.4 | 6558.7 ± | 1933.2 | 7020.8 ± | 1692.5 |
| AA metabolome | | | | | | | | |
| LXA$_4$ | — | | — | | — | | — | |
| AT-LXA$_4$ | 1.3 ± | 0.7 | 1.7 ± | 0.7 | 2.7 ± | 1.4 | 2.2 ± | 0.9 |
| LXB$_4$ | 0.5 ± | 0.5 | 1.0 ± | 0.8 | 0.4 ± | 0.4 | 0.6 ± | 0.5 |
| 5S,15S-diHETE | 0.5 ± | 0.3 | 0.7 ± | 0.4 | 1.2 ± | 0.6 | 1.3 ± | 0.7 |
| LTB$_4$ | 1.2 ± | 0.7 | 6.8 ± | 3.3 | 47.8 ± | 29.6 | 75.5 ± | 37.3 |
| 20-OH-LTB$_4$ | 0.2 ± | 0.1 | 0.7 ± | 0.4 | 2.6 ± | 1.4 | 8.2 ± | 4.4 |
| 5S,12S-diHETE | 1.2 ± | 0.9 | 1.3 ± | 0.8 | 3.7 ± | 2.0 | 3.4 ± | 1.8 |
| PGD$_2$ | 0.5 ± | 0.2 | 0.4 ± | 0.2 | 0.7 ± | 0.4 | 0.7 ± | 0.3 |
| PGE$_2$ | 0.3 ± | 0.1 | 0.6 ± | 0.3 | 0.7 ± | 0.3 | 0.9 ± | 0.3 |
| PGF$_{2a}$ | — | | 0.3 ± | 0.1 | 0.3 ± | 0.1 | 0.2 ± | 0.1 |

TABLE 6-continued

LM concentrations in human whole blood during coagulation in the presence of indomethacin. LC-MS-MS-based LM metabololipidomics analysis was performed with human blood collected at 0, 0.25, 0.5, 1, 3, 6, and 24 hours after coagulation in the presence of indomethacin. LM concentrations (pg/ml) are expressed as means ± SEM of six donors. (—) denotes concentrations <0.1 pg/ml.

| | | | | | | | | | | |
|---|---|---|---|---|---|---|---|---|---|---|
| TXB$_2$ | 1.4 | ± | 1.3 | 0.5 | ± | 0.3 | 1.0 | ± | 0.6 | 2.9 ± 1.5 |
| 15-HETE | 68.0 | ± | 30.0 | 97.7 | ± | 39.9 | 191.0 | ± | 86.3 | 303.6 ± 129.2 |
| 12-HETE | 1270.4 | ± | 509.6 | 2311.5 | ± | 876.6 | 3820.5 | ± | 1413.2 | 5159.5 ± 1175.0 |
| 5-HETE | 15.5 | ± | 8.1 | 19.7 | ± | 6.9 | 51.0 | ± | 21.3 | 61.4 ± 22.2 |
| AA | 6677.3 | ± | 2138.0 | 13096.4 | ± | 4734.3 | 17559.7 | ± | 6157.6 | 20436.6 ± 4293.6 |

| Mediator | Indomethacin t = 3 h | | Indomethacin t = 6 h | | Indomethacin t = 24 h | |
|---|---|---|---|---|---|---|
| | Avg | SEM | Avg | SEM | Avg | SEM |
| DHA metabolome | | | | | | |
| RvD1 | 1.8 ± | 0.8 | 5.6 ± | 2.3 | 34.2 ± | 10.6 |
| RvD2 | — | | — | | — | |
| RvD3 | — | | — | | — | |
| RvD4 | — | | — | | — | |
| RvD5 | 7.0 ± | 3.7 | 10.1 ± | 4.3 | 14.7 ± | 6.1 |
| RvD6 | — | | — | | — | |
| PD1 | 0.6 ± | 0.2 | 0.8 ± | 0.3 | 1.6 ± | 0.5 |
| 10S,17S-diHDHA | 1.5 ± | 0.6 | 3.6 ± | 1.2 | 5.5 ± | 1.9 |
| Maresin 1 | 1.4 ± | 0.8 | 1.8 ± | 1.2 | 4.8 ± | 2.8 |
| 7S,14S-diHDHA | 0.4 ± | 1.9 | 3.4 ± | 2.0 | 1.0 ± | 2.0 |
| 4S,14S-diHDHA | 9.0 ± | 4.4 | 12.2 ± | 4.7 | 15.7 ± | 7.0 |
| 17-HDHA | 62.7 ± | 22.6 | 95.8 ± | 24.2 | 179.7 ± | 35.1 |
| 14-HDHA | 987.4 ± | 328.3 | 1218.7 ± | 238.6 | 1492.9 ± | 223.7 |
| 7-HDHA | 3.6 ± | 1.0 | 4.3 ± | 0.9 | 6.2 ± | 1.6 |
| 4-HDHA | 17.1 ± | 4.7 | 26.6 ± | 5.8 | 42.3 ± | 11.8 |
| DHA | 85033.5 ± | 40114.6 | 84930.1 ± | 35684.3 | 108998.3 ± | 40268.0 |
| EPA metabolome | | | | | | |
| RvE1 | 0.3 ± | 0.2 | 0.8 ± | 0.3 | 4.5 ± | 2.6 |
| RvE2 | — | | — | | — | |
| RvE3 | — | | — | | — | |
| 18-HEPE | 301.2 ± | 138.8 | 393.8 ± | 139.8 | 721.1 ± | 223.1 |
| 15-HEPE | 238.4 ± | 95.2 | 339.7 ± | 109.5 | 504.7 ± | 124.1 |
| 12-HEPE | 11334.7 ± | 5155.4 | 12955.2 ± | 4868.2 | 16008.6 ± | 5342.6 |
| 5-HEPE | 13.1 ± | 4.2 | 15.0 ± | 2.0 | 23.3 ± | 3.3 |
| EPA | 10143.7 ± | 3677.5 | 13412.9 ± | 3960.6 | 17168.5 ± | 4455.6 |
| AA metabolome | | | | | | |
| LXA$_4$ | — | | — | | — | |
| AT-LXA$_4$ | 4.0 ± | 1.9 | 5.4 ± | 2.3 | 11.4 ± | 7.8 |
| LXB$_4$ | 0.7 ± | 0.6 | 0.8 ± | 0.6 | 2.0 ± | 1.7 |
| 5S,15S-diHETE | 4.2 ± | 2.0 | 8.0 ± | 3.3 | 14.4 ± | 7.5 |
| LTB$_4$ | 110.2 ± | 54.2 | 95.1 ± | 33.1 | 51.0 ± | 22.0 |
| 20-OH-LTB$_4$ | 14.0 ± | 6.5 | 20.2 ± | 12.0 | 21.3 ± | 14.1 |
| 5S,12S-diHETE | 12.1 ± | 5.4 | 14.4 ± | 5.4 | 19.0 ± | 8.4 |
| PGD$_2$ | 3.0 ± | 1.1 | 5.3 ± | 1.5 | 7.1 ± | 2.5 |
| PGE$_2$ | 1.2 ± | 0.4 | 1.8 ± | 0.4 | 2.6 ± | 1.0 |
| PGF$_{2a}$ | 0.5 ± | 0.2 | 0.7 ± | 0.2 | 1.6 ± | 0.7 |
| TXB$_2$ | 4.3 ± | 1.9 | 2.6 ± | 0.7 | 5.1 ± | 3.2 |
| 15-HETE | 694.4 ± | 249.2 | 1016.8 ± | 303.4 | 1498.0 ± | 306.1 |
| 12-HETE | 6782.9 ± | 2432.8 | 7205.4 ± | 2174.6 | 8564.0 ± | 2135.0 |
| 5-HETE | 122.6 ± | 41.0 | 145.2 ± | 32.4 | 148.7 ± | 37.8 |
| AA | 25625.0 ± | 9328.4 | 26651.4 ± | 8449.2 | 31800.5 ± | 8599.8 |

REFERENCES

1. J. Hunter, A Treatise on the *Blood, Inflammation, and Gun-Shot Wounds* (1794). (The Classics of Medicine Library, Special Ed., Birmingham, Ala., 1982).

2. R. De Caterina, n-3 fatty acids in cardiovascular disease. *N Engl J Med* 364, 2439-2450 (2011).

3. R. I. Handin, S. E. Lux, T. P. Stossel, Eds., *Blood: Principles and Practice of Hematology*, (Lippincott Williams & Wilkins, Philadelphia, 2003).

4. H. Z. Movat, in *Chemical Messengers of the Inflammatory Process*, J. C. Houck, Ed. (Elsevier/North-Holland Biomedical Press, Amsterdam, 1979), chap. 2.
5. S. L. Robbins, R. Cotran, *Pathologic Basis of Disease*. (W.B. Saunders Co., Philadelphia, ed. 2nd, 1979), pp. 1598.
6. B. Samuelsson, M. Goldyne, E. Granstrom, M. Hamberg, S. Hammarstrom, C. Malmsten, Prostaglandins and thromboxanes. *Annu Rev Biochem* 47, 997-1029 (1978).
7. J. Z. Haeggstrom, C. D. Funk, Lipoxygenase and leukotriene pathways: biochemistry, biology, and roles in disease. *Chem Rev* 111, 5866-5898 (2011).
8. C. N. Serhan, Pro-resolving lipid mediators are leads for resolution physiology. *Nature* 510, 92-101 (2014).
9. R. Medzhitov, Origin and physiological roles of inflammation. *Nature* 454, 428-435 (2008).
10. C. Nathan, Fresh approaches to anti-infective therapies. *Sci Transl Med* 4, 140sr142 (2012).
11. M. J. Delano, P. A. Ward, Sepsis-induced immune dysfunction: can immune therapies reduce mortality? *J Clin Invest* 126, 23-31 (2016).
12. J. N. Fullerton, D. W. Gilroy, Resolution of inflammation: a new therapeutic frontier. *Nat Rev Drug Discov* 15, 551-567 (2016).
13. J. Dalli, J. W. Winkler, R. A. Colas, H. Amardottir, C. Y. C. Cheng, N. Chiang, N. A. Petasis, C. N. Serhan, Resolvin D3 and aspirin-triggered resolvin D3 are potent immunoresolvents. *Chem. Biol.* 20, 188-201 (2013).
14. J. Claria, J. Dalli, S. Yacoubian, F. Gao, C. N. Serhan, Resolvin D1 and resolvin D2 govern local inflammatory tone in obese fat. *J Immunol* 189, 2597-2605 (2012).
15. R. A. Colas. M. Shinohara, J. Dalli, N. Chiang, C. N. Serhan, Identification and signature profiles for pro-resolving and inflammatory lipid mediators in human tissue. *Am J Physiol Cell Physiol* 307, C39-54 (2014).
16. A. E. Barden, E. Mas, T. A. Mori, n-3 Fatty acid supplementation and proresolving mediators of inflammation. *Curr. Opin. Lipidol.* 27, 26-32 (2016).
17. A. E. Barden, M. Moghaddami, E. Mas, M. Phillips, L. G. Cleland, T. A. Mori, Specialised pro-resolving mediators of inflammation in inflammatory arthritis. *Prostaglandins Leukot. Essent. Fatty Acids* 107, 24-29 (2016).
18. S. Bohr, S. J. Patel, D. Sarin, D. Irimia, M. L Yarmush, F. Berthiaume, Resolvin D2 prevents secondary thrombosis and necrosis in a mouse burn wound model. *Wound Repair Regen.* 21, 35-43 (2013).
19. N. H. Pope, M. Salmon, J. P. Davis, A. Chatterjee, G. Su, M. S. Conte, G. Ailawadi, G. R. Upchurch, Jr., D-series resolvins inhibit murine abdominal aortic aneurysm formation and increase M2 macrophage polarization. *FASEB J.* 30, 4192-4201 (2016).
20. M. Hamberg, J. Svensson, B. Samuelsson, Thromboxanes: a new group of biologically active compounds derived from prostaglandin endoperoxides. *Proc. Natl. Acad. Sci. U.S.A* 72, 2994-2998 (1975).
21. E. Krump, S. Picard, J. Mancini, P. Borgeat, Suppression of leukotriene $B_4$ biosynthesis by endogenous adenosine in ligand-activated human neutrophils. *J. Exp. Med.* 186, 1401-1406 (1997).
22. A. J. Marcus, M. J. Broekman, J. H. Drosopoulos, N. Islam, D. J. Pinsky, C. Sesti, R. Levi, Heterologous cell-cell interactions: thromboregulation, cerebroprotection and cardioprotection by CD39 (NTPDase-1). *J Thromb Haemost* 1, 2497-2509 (2003).
23. C. N. Serhan, K. A. Sheppard, Lipoxin formation during human neutrophil-platelet interactions. Evidence for the transformation of leukotriene $A_4$ by platelet 12-lipoxygenase in vitro. *J. Clin. Invest.* 85, 772-780 (1990).
24. R. E. Abdulnour, J. Dalli, J. K. Colby, N. Krishnamoorthy, J. Y. Timmons, S. H. Tan, R. A. Colas, N. A. Petasis, C. N. Serhan, B. D. Levy, Maresin 1 biosynthesis during platelet-neutrophil interactions is organ-protective. *Proc. Natl. Acad. Sci. U.S.A* 111, 16526-16531 (2014).
25. B. Deng, C. W. Wang, H. H. Amardottir, Y. Li, C. Y. Cheng, J. Dalli, C. N. Serhan, Maresin biosynthesis and identification of maresin 2, a new anti-inflammatory and pro-resolving mediator from human macrophages. *PLoS One* 9, e102362 (2014).
26. V. Brancaleone, T. Gobbetti. N. Cenac, P. le Faoudier, B. Colom, R. J. Flower, N. Vergnolle, S. Nourshargh, M. Perretti, A vasculo-protective circuit centred on Lipoxin A4 and aspirin-triggered 15-epi-lipoxin A4 operative in murine microcirculation. *Blood*, 10.1182/blood-2013-1104-496661 [doi] (2013).
27. M. J. Stables, J. Newson, S. S. Ayoub, J. Brown, C. J. Hyams, D. W. Gilroy, Priming innate immune responses to infection by cydooxygenase inhibition kills antibiotic-susceptible and -resistant bacteria. *Blood* 116, 2950-2959 (2010).
28. K. Sekiya, H. Okuda, Selective inhibition of platelet lipoxygenase by baicalein. *Biochem. Biophys. Res. Commun.* 105, 1090-1095 (1982).
29. J. M. Schwab, N. Chiang, M. Arita, C. N. Serhan, Resolvin E1 and protectin D1 activate inflammation-resolution programmes. *Nature* 447, 869-874 (2007).
30. M. Spite, L. V. Norling, L. Summers, R. Yang, D. Cooper, N. A. Petasis, R. J. Flower, M. Perretti, C. N. Serhan, Resolvin D2 is a potent regulator of leukocytes and controls microbial sepsis. *Nature* 461, 1287-1291 (2009).
31. B. Gaudilliere, G. K. Fragiadakis, R. V. Bruggner, M. Nicolau, R. Finck, M. Tingle, J. Silva, E. A. Ganio, C. G. Yeh, W. J. Maloney, J. I. Huddleston, S. B. Goodman, M. M. Davis, S. C. Bendall, W. J. Fanti, M. S. Angst, G. P. Nolan, Clinical recovery from surgery correlates with single-cell immune signatures. *Sci Transi Med* 6, 255ra131 (2014).
32. G. Fredman, C. N. Serhan, Specialized proresolving mediator targets for RvE1 and RvD1 in peripheral blood and mechanisms of resolution. *Biochem J* 437, 185-197 (2011).
33. A. D. Amir el, K. L. Davis, M. D. Tadmor, E. F. Simonds, J. H. Levine, S. C. Bendall, D. K. Shenfeld, S. Krishnaswamy, G. P. Nolan, D. Pe'er, viSNE enables visualization of high dimensional single-cell data and reveals phenotypic heterogeneity of leukemia. *Nat Biotechnol* 31, 545-552 (2013).
34. S. Massberg, L. Grahl, M. L. von Bruehl, D. Manukyan, S. Pfeiler. C. Goosmann, V. Brinkmann, M. Lorenz, K. Bidzhekov, A. B. Khandagale, I. Konrad, E. Kennerknecht, K. Reges, S. Holdenrieder, S. Braun, C. Reinhardt, M. Spannagl, K. T. Preissner, B. Engelmann, Reciprocal coupling of coagulation and innate immunity via neutrophil serine proteases. *Nat. Med.* 16, 887-896 (2010).
35. Z. Gu, G. J. Lamont, R. J. Lamont, S. M. Uriarte, H. Wang, D. A. Scott, Resolvin D1, resolvin D2 and maresin 1 activate the GSK3beta anti-inflammatory axis in TLR4-engaged human monocytes. *Innate Immun* 22, 186-195 (2016).
36. V. Chiurchiu, A. Leuti, J. Dalli, A. Jacobsson, L. Battistini, M. Maccarrone, C. N. Serhan, Proresolving lipid mediators resolvin D1, resolvin D2, and maresin 1 are critical in modulating T cell responses. *Sci Transl Med* 8, 353ra111 (2016).
37. S. Endres, R. Ghorbani, V. E. Kelley, K. Georgilis, G. Lonnemann, J. W. van der Meer, J. G. Cannon, T. S. Rogers, M. S. Klempner, P. C. Weber, et al., The effect of dietary supplementation with n-3 polyunsaturated fatty acids on the synthesis of interleukin-1 and tumor necrosis factor by mononuclear cells. *N Engl J Med* 320, 265-271 (1989).
38. E. Mas, K. D. Croft, P. Zahra, A. Barden, T. A. Mori, Resolvins D1, D2, and other mediators of self-limited resolution of inflammation in human blood following n-3 fatty acid supplementation. *Clin. Chem.* 58, 1476-1484 (2012).
39. L. C. Del Gobbo, F. Imamura, S. Aslibekyan, M. Marklund, J. K. Virtanen, M. Wennberg, M. Y. Yakoob, S. E. Chiuve, L. Dela Cruz, A. C. Frazier-Wood, A. M. Fretts, E. Guallar, C. Matsumoto, K. Prem, T. Tanaka, J. H. Wu, X. Zhou, C. Helmer, E. Ingelsson, J. M. Yuan, P. Barberger-Gateau, H. Campos, P. H. Chaves, L. Djousse, G. G. Giles, J. Gomez-Aracena, A. M. Hodge, F. B. Hu, J. H. Jansson, I. Johansson, K. T. Khaw, W. P. Koh, R. N. Lemaitre, L. Lind, R. N. Luben, E. B. Rimm, U. Riserus, C. Samieri, P. W. Franks, D. S. Siscovick, M. Stampfer, L. M. Steffen, B. T. Steffen, M. Y. Tsai, R. M. van Dam, S. Voutilainen, W. C. Willett, M. Woodward, D. Mozaffarian, omega-3 Polyunsaturated Fatty Acid Biomarkers and Coronary Heart Disease: Pooling Project of 19 Cohort Studies. *JAMA Intern Med* 176, 1155-1166 (2016).
40. A. Sekikawa, L. Steingrimsdottir, H. Ueshima, C. Shin, J. D. Curb, R. W. Evans, A. M. Hauksdottir, A. Kadota, J. Choo, K. Masaki, B. Thorsson, L. J. Launer, M. E. Garcia, H. Maegawa, B. J. Willcox, G. Eiriksdottir, A. Fujiyoshi, K. Miura, T. B. Harris, L. H. Kuller, V. Gudnason, Serum levels of marine-derived n-3 fatty acids in Icelanders, Japanese, Koreans, and Americans—a descriptive epidemiologic study. *Prostaglandins Leukot Essent Fatty Acids* 87, 11-16 (2012).
41. H. Uno, K. Furukawa, D. Suzuki, H. Shimizu, M. Ohtsuka, A. Kato, H. Yoshitomi, M. Miyazaki, Immunonutrition suppresses acute inflammatory responses through modulation of resolvin E1 in patients undergoing major hepatobiliary resection. *Surgery* 160, 228-236 (2016).
42. C. R. Lee, D. C. Zeldin, Resolvin Infectious Inflammation by Targeting the Host Response. *N. Engl. J. Med.* 373, 2183-2185 (2015).
43. J. K. Baillie, P. Digard, Influenza-time to target the host? *N. Engl. J. Med.* 369, 191-193 (2013).
44. I. Tabas, K. E. Bomfeldt, Macrophage Phenotype and Function in Different Stages of Atherosclerosis. *Circ Res* 118, 653-667 (2016).
45. B. E. Sansbury, M. Spite, Resolution of Acute Inflammation and the Role of Resolvins in Immunity, Thrombosis, and Vascular Biology. *Circ Res* 119, 113-130 (2016).
46. G. P. Pidgeon, J. Lysaght, S. Krishnamoorthy, J. V. Reynolds, K. O'Byme, D. Nie, K. V. Honn, Lipoxygenase metabolism: roles in tumor progression and survival. *Cancer Metastasis Rev* 26, 503-524 (2007).
47. C. N. Serhan, G. Fredman, R. Yang, S. Karamnov, L. S. Belayev, N. G. Bazan, M. Zhu, J. W. Winkler, N. A. Petasis, Novel proresolving aspirin-triggered DHA pathway. *Chem. Biol.* 18, 976-987 (2011).
48. J. W. Winkler, S. K. Orr, J. Dalli, C. Y. Cheng, J. M. Sanger, N. Chiang, N. A. Petasis, C. N. Serhan, Resolvin D4 stereoassignment and its novel actions in host protection and bacterial clearance. *Sci Rep* 6, 18972 (2016).
49. J. N. Topper, J. Cai, D. Falb, M. A. Gimbrone, Jr., Identification of vascular endothelial genes differentially responsive to fluid mechanical stimuli: Cyclooxygenase-2, manganese superoxide dismutase, and endothelial cell nitric oxide synthase are selectively up-regulated by steady laminar shear stress. *Proc. Natl. Acad. Sci USA* 93, 10417-10422 (1996).
50. C. N. Serhan, C. B. Clish, J. Brannon, S. P. Colgan, N. Chiang, K. Gronert, Novel functional sets of lipid-derived mediators with antiinflammatory actions generated from omega-3 fatty acids via cyclooxygenase 2-nonsteroidal antiinflammatory drugs and transcellular processing. *J. Exp. Med.* 192, 1197-1204 (2000).
51. M. Roqueta-Rivera, C. K. Stroud, W. M. Haschek, S. J. Akare, M. Segre, R. S. Brush, M. P. Agbaga, R. E. Anderson, R. A. Hess, M. T. Nakamura, Docosahexaenoic acid supplementation fully restores fertility and spermatogenesis in male delta-6 desaturase-null mice. *J. Lipid Res.* 51, 360-367 (2010).
52. T. Minamino, M. Kitakaze, H. Asanuma, Y. Tomiyama, M. Shiraga, H. Sato, Y. Ueda, H. Funaya, T. Kuzuya, Y. Matsuzawa, M. Hori, Endogenous adenosine inhibits P-selectin-dependent formation of coronary thromboemboli during hypoperfusion in dogs. *J. Clin. Invest.* 101, 1643-1653 (1998).
53. T. K. Elajami, R. A. Colas, J. Dalli, N. Chiang, C. N. Serhan, F. K. Welty, Specialized proresolving lipid mediators in patients with coronary artery disease and their potential for clot remodeling. *FASEB J.* 30, 2792-2801 (2016).
54. R. Liu, Y. Ye, L. Qiang, X. Liao, Y. Zhao, The fragmentation pathway of the nucleosides under the electrospray ionization multi-stage mass spectrometry. *Life Sci. J.* 5, 37-40 (2008).
55. B. Bodenmiller, E. R. Zunder, R. Finck, T. J. Chen, E. S. Savig, R. V. Bruggner, E. F. Simonds, S. C. Bendall, K. Sachs, P. O. Krutzik, G. P. Nolan, Multiplexed mass cytometry profiling of cellular states perturbed by small-molecule regulators. *Nat Biotechnol* 30, 858-867 (2012).

The citation of any document is not to be construed as an admission that it is prior art with respect to the present invention.

The present invention has been described in terms of one or more preferred embodiments, and it should be appreciated that many equivalents, alternatives, variations, and modifications, aside from those expressly stated, are possible and within the scope of the invention.

We claim:

1. A method of providing a metabololipidomic profile and SPM signature on the progress of the innate host defense response following blood clotting comprising the steps of
   (a) taking one or more measurements in a patient's blood sample, wherein the sample is whole blood obtained during the time-course of clotting or coagulation or following clotting or coagulation, of pro-thrombotic and pro-inflammatory mediators and specialized proresolving mediators (SPMs),
   (b) removing adenosine ex vivo, wherein the removal of adenosine occurs before taking the one or more measurements;
   wherein a personalized metabololipidomic profile is obtained.

2. The method of claim 1 additionally comprising the step of (c) comparing the one or more measurements to that taken from normal or reference blood, thereby developing a comparison profile.

3. The method of claim 2 additionally comprising the step of (d) wherein the profile of claim 1 is used to make a medical or therapeutic decision.

4. The method of claim 3, wherein the medical or therapeutic decision is a diagnosis of at least one of a disease, illness, disorder, or health deficiency.

5. The method of claim 1, wherein the clotting or coagulation is initiated by placing the sample in contact with a negatively charged surface.

6. The method of claim 1, wherein the sample is permeabilized by freeze-thaw to release the pro-thrombotic and pro-inflammatory mediators and the SPMs, wherein this permeabilization step occurs prior to the taking of the one or more measurements.

7. The method of claim 6, wherein the released pro-thrombotic and pro-inflammatory mediators and the SPMs are purified prior to the taking of the one or more measurements.

8. The method of claim 7, wherein the released pro-thrombotic and pro-inflammatory mediators and the SPMs are purified by adding an agent to remove proteins.

9. The method of claim 7, wherein the released pro-thrombotic and pro-inflammatory mediators and the SPMs are purified by solid-phase extraction.

10. The method of claim 1, wherein the one or more measurements is taken via liquid chromatography-tandem mass spectrometry.

11. The method of claim 1, wherein the metabololipodomic profile comprises an initial appearance of the pro-inflammatory mediators TXB2, $LTB_4$, and $PGD_2$ following clotting and the later appearance of the specific SPM-containing cluster.

12. The method of claim 11, wherein the specific SPM cluster comprises RvE1, RvD5, RvD1, MaR1 and $LXB_4$.

13. The method of claim 12, wherein the specific SPM cluster is enhanced in the metabololipodomic profile specific cluster and a second SPM cluster is unmasked and is represented in the profile.

14. The method of claim 13, wherein the second SPM cluster, unmasked by removal of adenosine, comprises RvD3, RvD4 and RvD6.

15. The method of claim 1, wherein adenosine is removed by incubation of the sample with addition of adenosine deaminase.

16. The method of claim 15, wherein adenosine deaminase is used at a concentration of 200 mU per 4 mls of whole blood.

* * * * *